US012594171B2

(12) United States Patent
Yadav et al.

(10) Patent No.: US 12,594,171 B2
(45) Date of Patent: *Apr. 7, 2026

(54) ROBOTIC SYSTEM FOR SHOULDER ARTHROPLASTY USING STEMLESS IMPLANT COMPONENTS

(71) Applicant: Howmedica Osteonics Corp., Mahwah, NJ (US)

(72) Inventors: Rajan Yadav, New Delhi (IN); Jetinder Singh, Gurgaon (IN); Koustubh Rao, Hallandale Beach, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 765 days.

This patent is subject to a terminal disclaimer.

(21) Appl. No.: 17/500,182

(22) Filed: Oct. 13, 2021

(65) Prior Publication Data

US 2022/0031413 A1 Feb. 3, 2022

Related U.S. Application Data

(63) Continuation of application No. 16/181,766, filed on Nov. 6, 2018, now Pat. No. 11,173,048.

(Continued)

(51) Int. Cl.
*A61B 34/20* (2016.01)
*A61B 17/16* (2006.01)
(Continued)

(52) U.S. Cl.
CPC ............ *A61F 2/4612* (2013.01); *A61B 34/10* (2016.02); *A61B 34/20* (2016.02); *A61B 34/30* (2016.02);
(Continued)

(58) Field of Classification Search
CPC .... A61F 2/4612; A61B 17/14; A61B 17/1684
See application file for complete search history.

(56) References Cited

U.S. PATENT DOCUMENTS

| 5,824,085 A | 10/1998 | Sahay et al. |
| 6,002,859 A | 12/1999 | DiGioia, III et al. |

(Continued)

FOREIGN PATENT DOCUMENTS

| WO | 2009057964 A2 | 5/2009 |
| WO | 2010068212 A1 | 6/2010 |

(Continued)

OTHER PUBLICATIONS

Arthrex, Inc., "Partial Eclipse Stemless Shoulder Arthroplasty Brochure", 2016, 12 pages.

(Continued)

*Primary Examiner* — Tracy L Kamikawa
(74) *Attorney, Agent, or Firm* — Howard & Howard Attorneys PLLC

(57) ABSTRACT

Robotic systems and methods for robotic arthroplasty. The robotic system includes a machining station and a guidance station. The guidance station tracks movement of various objects in the operating room, such as a surgical tool, a humerus of a patient, and a scapula of the patient. The guidance station tracks these objects for purposes of controlling movement of the surgical tool relative to virtual cutting boundaries or other virtual objects associated with the humerus and scapula to facilitate preparation of bone to receive a shoulder implant system. The virtual objects are located based on density data of the bone such that, when one or more shoulder implants are fully seated in the bone, distal portions of the implants are located in a first region of the bone having a density characteristic greater than an adjacent second region of the bone.

19 Claims, 9 Drawing Sheets

Related U.S. Application Data

(60) Provisional application No. 62/582,624, filed on Nov. 7, 2017.

(51) Int. Cl.

| | |
|---|---|
| *A61B 34/00* | (2016.01) |
| *A61B 34/10* | (2016.01) |
| *A61B 34/30* | (2016.01) |
| *A61B 34/32* | (2016.01) |
| *A61F 2/46* | (2006.01) |
| *B25J 9/16* | (2006.01) |
| *A61B 17/14* | (2006.01) |
| *A61B 90/00* | (2016.01) |

(52) U.S. Cl.

CPC .............. *A61B 34/32* (2016.02); *A61B 34/76* (2016.02); *B25J 9/1666* (2013.01); *B25J 9/1676* (2013.01); *A61B 17/14* (2013.01); *A61B 17/164* (2013.01); *A61B 17/1659* (2013.01); *A61B 17/1684* (2013.01); *A61B 2034/102* (2016.02); *A61B 2034/105* (2016.02); *A61B 2034/107* (2016.02); *A61B 2034/108* (2016.02); *A61B 2034/2055* (2016.02); *A61B 2034/2057* (2016.02); *A61B 2034/2065* (2016.02); *A61B 2034/2068* (2016.02); *A61B 2090/0801* (2016.02); *A61F 2002/4633* (2013.01); *G05B 2219/35021* (2013.01); *G05B 2219/45168* (2013.01)

(56) References Cited

U.S. PATENT DOCUMENTS

| | | | |
|---|---|---|---|
| RE36,974 | E | 11/2000 | Bonutti |
| 6,205,411 | B1 | 3/2001 | DiGioia, III et al. |
| 6,500,195 | B2 | 12/2002 | Bonutti |
| 6,702,821 | B2 | 3/2004 | Bonutti |
| 6,770,078 | B2 | 8/2004 | Bonutti |
| 7,104,996 | B2 | 9/2006 | Bonutti |
| 7,206,626 | B2 | 4/2007 | Quaid, III |
| 7,206,627 | B2 | 4/2007 | Abovitz et al. |
| 7,468,075 | B2 | 12/2008 | Lang et al. |
| 7,510,557 | B1 | 3/2009 | Bonutti |
| 7,534,263 | B2 | 5/2009 | Burdulis, Jr. et al. |
| 7,615,054 | B1 | 11/2009 | Bonutti |
| 7,618,451 | B2 | 11/2009 | Berez et al. |
| 7,635,390 | B1 | 12/2009 | Bonutti |
| 7,708,740 | B1 | 5/2010 | Bonutti |
| 7,708,741 | B1 | 5/2010 | Bonutti |
| 7,725,162 | B2 | 5/2010 | Malackowski et al. |
| 7,747,311 | B2 | 6/2010 | Quaid, III |
| 7,749,229 | B1 | 7/2010 | Bonutti |
| 7,806,896 | B1 | 10/2010 | Bonutti |
| 7,806,897 | B1 | 10/2010 | Bonutti |
| 7,828,852 | B2 | 11/2010 | Bonutti |
| 7,831,292 | B2 | 11/2010 | Quaid et al. |
| 7,837,736 | B2 | 11/2010 | Bonutti |
| 7,892,236 | B1 | 2/2011 | Bonutti |
| 7,931,690 | B1 | 4/2011 | Bonutti |
| 7,959,635 | B1 | 6/2011 | Bonutti |
| 7,981,158 | B2 | 7/2011 | Fitz et al. |
| 8,010,180 | B2 * | 8/2011 | Quaid .................... A61B 34/71 600/426 |
| 8,014,984 | B2 | 9/2011 | Iannotti et al. |
| 8,066,708 | B2 | 11/2011 | Lang et al. |
| 8,083,745 | B2 | 12/2011 | Lang et al. |
| 8,095,200 | B2 | 1/2012 | Quaid, III |
| 8,105,330 | B2 | 1/2012 | Fitz et al. |
| 8,122,582 | B2 | 2/2012 | Burdulis, Jr. et al. |
| 8,133,229 | B1 | 3/2012 | Bonutti |
| 8,234,097 | B2 | 7/2012 | Steines et al. |
| 8,277,454 | B2 | 10/2012 | Neubauer et al. |
| 8,287,522 | B2 | 10/2012 | Moses et al. |
| 8,337,501 | B2 | 12/2012 | Fitz et al. |
| 8,337,507 | B2 | 12/2012 | Lang et al. |
| 8,337,508 | B2 | 12/2012 | Lavallee et al. |
| 8,343,218 | B2 | 1/2013 | Lang et al. |
| 8,361,163 | B2 | 1/2013 | Quaid |
| 8,366,771 | B2 | 2/2013 | Burdulis, Jr. et al. |
| 8,377,129 | B2 | 2/2013 | Fitz et al. |
| 8,380,471 | B2 | 2/2013 | Iannotti et al. |
| 8,391,954 | B2 | 3/2013 | Quaid, III |
| 8,425,522 | B2 | 4/2013 | Bonutti |
| 8,439,926 | B2 | 5/2013 | Bojarski et al. |
| 8,439,978 | B2 | 5/2013 | Ebbitt |
| 8,457,719 | B2 | 6/2013 | Moctezuma de la Barrera et al. |
| 8,460,304 | B2 | 6/2013 | Fitz et al. |
| 8,480,754 | B2 | 7/2013 | Bojarski et al. |
| 8,498,744 | B2 | 7/2013 | Odermatt et al. |
| 8,500,740 | B2 | 8/2013 | Bojarski et al. |
| 8,529,630 | B2 | 9/2013 | Bojarski et al. |
| 8,551,099 | B2 | 10/2013 | Lang et al. |
| 8,551,102 | B2 | 10/2013 | Fitz et al. |
| 8,551,103 | B2 | 10/2013 | Fitz et al. |
| 8,551,169 | B2 | 10/2013 | Fitz et al. |
| 8,556,906 | B2 | 10/2013 | Fitz et al. |
| 8,556,907 | B2 | 10/2013 | Fitz et al. |
| 8,556,971 | B2 | 10/2013 | Lang |
| 8,556,983 | B2 | 10/2013 | Bojarski et al. |
| 8,561,278 | B2 | 10/2013 | Fitz et al. |
| 8,562,611 | B2 | 10/2013 | Fitz et al. |
| 8,562,618 | B2 | 10/2013 | Fitz et al. |
| 8,568,479 | B2 | 10/2013 | Fitz et al. |
| 8,568,480 | B2 | 10/2013 | Fitz et al. |
| 8,585,708 | B2 | 11/2013 | Fitz et al. |
| 8,617,172 | B2 | 12/2013 | Fitz et al. |
| 8,623,026 | B2 | 1/2014 | Wong et al. |
| 8,623,030 | B2 | 1/2014 | Bonutti |
| 8,632,552 | B2 | 1/2014 | Bonutti |
| 8,641,660 | B2 | 2/2014 | Bonutti et al. |
| 8,641,716 | B2 | 2/2014 | Fitz et al. |
| 8,641,726 | B2 | 2/2014 | Bonutti |
| 8,657,827 | B2 | 2/2014 | Fitz et al. |
| 8,690,945 | B2 | 4/2014 | Fitz et al. |
| 8,709,016 | B2 | 4/2014 | Park et al. |
| 8,731,885 | B2 | 5/2014 | Iannotti et al. |
| 8,753,346 | B2 | 6/2014 | Suarez et al. |
| 8,753,402 | B2 * | 6/2014 | Winslow .............. A61F 2/4003 623/22.17 |
| 8,768,028 | B2 | 7/2014 | Lang et al. |
| 8,771,365 | B2 | 7/2014 | Bojarski et al. |
| 8,784,495 | B2 | 7/2014 | Bonutti |
| 8,801,719 | B2 | 8/2014 | Park et al. |
| 8,801,720 | B2 | 8/2014 | Park et al. |
| 8,834,490 | B2 | 9/2014 | Bonutti |
| 8,840,629 | B2 | 9/2014 | Bonutti |
| 8,858,557 | B2 | 10/2014 | Bonutti |
| 8,882,779 | B2 | 11/2014 | Park et al. |
| 8,906,107 | B2 | 12/2014 | Bojarski et al. |
| 8,911,499 | B2 | 12/2014 | Quaid et al. |
| 8,926,706 | B2 | 1/2015 | Bojarski et al. |
| 8,936,596 | B2 | 1/2015 | Mittelstadt et al. |
| 8,951,259 | B2 | 2/2015 | Fitz et al. |
| 8,974,539 | B2 | 3/2015 | Bojarski et al. |
| 8,977,021 | B2 | 3/2015 | Kang et al. |
| 8,979,859 | B2 | 3/2015 | Leparmentier et al. |
| 8,992,542 | B2 | 3/2015 | Hagag et al. |
| 8,998,915 | B2 | 4/2015 | Fitz et al. |
| 9,002,426 | B2 | 4/2015 | Quaid et al. |
| 9,008,757 | B2 | 4/2015 | Wu |
| 9,020,788 | B2 | 4/2015 | Lang et al. |
| 9,023,050 | B2 | 5/2015 | Lang et al. |
| 9,055,953 | B2 | 6/2015 | Lang et al. |
| 9,060,797 | B2 | 6/2015 | Bonutti |
| 9,066,728 | B2 | 6/2015 | Burdulis, Jr. et al. |
| 9,072,531 | B2 | 7/2015 | Fitz et al. |
| 9,084,617 | B2 | 7/2015 | Lang et al. |
| 9,095,353 | B2 | 8/2015 | Burdulis, Jr. et al. |
| 9,101,394 | B2 | 8/2015 | Arata et al. |
| 9,101,443 | B2 | 8/2015 | Bonutti |
| 9,107,679 | B2 | 8/2015 | Lang et al. |
| 9,107,680 | B2 | 8/2015 | Fitz et al. |

(56) References Cited

U.S. PATENT DOCUMENTS

| | | | |
|---|---|---|---|
| 9,113,921 | B2 | 8/2015 | Lang et al. |
| 9,119,655 | B2 | 9/2015 | Bowling et al. |
| 9,125,672 | B2 | 9/2015 | Fitz et al. |
| 9,125,673 | B2 | 9/2015 | Fitz et al. |
| 9,125,753 | B2 | 9/2015 | Caballes |
| 9,131,597 | B2 | 9/2015 | Taft et al. |
| 9,149,281 | B2 | 10/2015 | Bonutti |
| 9,155,544 | B2 | 10/2015 | Bonutti |
| 9,186,161 | B2 | 11/2015 | Lang et al. |
| 9,192,395 | B2 | 11/2015 | Bonutti |
| 9,192,459 | B2 | 11/2015 | Bonutti |
| 9,216,025 | B2 | 12/2015 | Fitz et al. |
| 9,220,510 | B2 | 12/2015 | Cheal et al. |
| 9,220,516 | B2 | 12/2015 | Lang et al. |
| 9,220,517 | B2 | 12/2015 | Lang et al. |
| 9,226,828 | B2 | 1/2016 | Bonutti |
| 9,241,724 | B2 | 1/2016 | Lang et al. |
| 9,241,725 | B2 | 1/2016 | Lang et al. |
| 9,265,509 | B2 | 2/2016 | Park et al. |
| 9,271,766 | B2 | 3/2016 | Bonutti |
| 9,275,192 | B2 | 3/2016 | Kang et al. |
| 9,289,264 | B2 | 3/2016 | Iorgulescu et al. |
| 9,292,657 | B2 | 3/2016 | Kang et al. |
| 9,295,481 | B2 | 3/2016 | Fitz et al. |
| 9,295,482 | B2 | 3/2016 | Fitz et al. |
| 9,308,005 | B2 | 4/2016 | Fitz et al. |
| 9,308,053 | B2 | 4/2016 | Bojarski et al. |
| 9,314,256 | B2 | 4/2016 | Fitz et al. |
| 9,320,620 | B2 | 4/2016 | Bojarski et al. |
| 9,326,780 | B2 | 5/2016 | Wong et al. |
| 9,358,018 | B2 | 6/2016 | Fitz et al. |
| 9,364,291 | B2 | 6/2016 | Bellettre et al. |
| 9,375,222 | B2 | 6/2016 | Fitz et al. |
| 9,381,025 | B2 | 7/2016 | Fitz et al. |
| 9,381,085 | B2 | 7/2016 | Axelson, Jr. et al. |
| 9,387,079 | B2 | 7/2016 | Bojarski et al. |
| 9,402,726 | B2 | 8/2016 | Linderman et al. |
| 9,408,615 | B2 | 8/2016 | Fitz et al. |
| 9,439,767 | B2 | 9/2016 | Bojarski et al. |
| 9,474,847 | B2 | 10/2016 | Bonutti et al. |
| 9,486,227 | B2 | 11/2016 | Bonutti |
| 9,492,237 | B2 | 11/2016 | Kang et al. |
| 9,495,483 | B2 | 11/2016 | Steines et al. |
| 9,545,268 | B2 | 1/2017 | Bonutti |
| 9,579,110 | B2 | 2/2017 | Bojarski et al. |
| 9,579,129 | B2 | 2/2017 | Bonutti |
| 9,585,725 | B2 | 3/2017 | Bonutti |
| 9,588,587 | B2 | 3/2017 | Otto et al. |
| 9,597,157 | B2 | 3/2017 | Hagag et al. |
| 9,603,711 | B2 | 3/2017 | Bojarski et al. |
| 9,610,084 | B2 | 4/2017 | Walker |
| 9,629,687 | B2 | 4/2017 | Bonutti |
| 9,636,185 | B2 | 5/2017 | Quaid et al. |
| 9,655,683 | B2 | 5/2017 | Iorgulescu et al. |
| 9,665,686 | B2 | 5/2017 | Van Vorhis et al. |
| 9,687,308 | B2 | 6/2017 | Windolf et al. |
| 11,173,048 | B2 * | 11/2021 | Yadav .................... A61B 34/10 |
| 2002/0016634 | A1 * | 2/2002 | Maroney ............ A61B 17/1659 |
| | | | 623/22.42 |
| 2003/0055502 | A1 | 3/2003 | Lang et al. |
| 2006/0089646 | A1 | 4/2006 | Bonutti |
| 2006/0142657 | A1 | 6/2006 | Quaid et al. |
| 2007/0066917 | A1 | 3/2007 | Hodorek et al. |
| 2007/0179626 | A1 | 8/2007 | de la Barrera et al. |
| 2008/0004633 | A1 | 1/2008 | Arata et al. |
| 2008/0010705 | A1 | 1/2008 | Quaid et al. |
| 2008/0058945 | A1 | 3/2008 | Hajaj et al. |
| 2009/0000626 | A1 | 1/2009 | Quaid et al. |
| 2009/0012532 | A1 | 1/2009 | Quaid et al. |
| 2009/0157192 | A1 | 6/2009 | Stuart |
| 2010/0106194 | A1 | 4/2010 | Bonutti et al. |
| 2010/0153081 | A1 | 6/2010 | Bellettre et al. |
| 2010/0217400 | A1 | 8/2010 | Nortman et al. |
| 2010/0329530 | A1 | 12/2010 | Lang et al. |
| 2011/0054624 | A1 | 3/2011 | Iannotti |

| | | | |
|---|---|---|---|
| 2011/0060375 | A1 | 3/2011 | Bonutti |
| 2011/0071528 | A1 | 3/2011 | Carson |
| 2011/0071529 | A1 | 3/2011 | Carson |
| 2011/0071530 | A1 | 3/2011 | Carson |
| 2011/0071531 | A1 | 3/2011 | Carson |
| 2011/0071532 | A1 | 3/2011 | Carson |
| 2011/0071645 | A1 | 3/2011 | Bojarski et al. |
| 2011/0082587 | A1 | 4/2011 | Ziaei et al. |
| 2011/0213374 | A1 | 9/2011 | Fitz et al. |
| 2011/0213377 | A1 | 9/2011 | Lang et al. |
| 2011/0213428 | A1 | 9/2011 | Fitz et al. |
| 2011/0213429 | A1 | 9/2011 | Lang et al. |
| 2011/0238073 | A1 | 9/2011 | Lang et al. |
| 2011/0313423 | A1 | 12/2011 | Lang et al. |
| 2012/0010623 | A1 | 1/2012 | Bonutti |
| 2012/0059378 | A1 | 3/2012 | Farrell |
| 2012/0066892 | A1 | 3/2012 | Lang et al. |
| 2012/0071883 | A1 | 3/2012 | Lang et al. |
| 2012/0109150 | A1 | 5/2012 | Quaid et al. |
| 2012/0109152 | A1 | 5/2012 | Quaid, III |
| 2012/0191205 | A1 | 7/2012 | Bojarski et al. |
| 2012/0191420 | A1 | 7/2012 | Bojarski et al. |
| 2012/0197408 | A1 | 8/2012 | Lang et al. |
| 2012/0215226 | A1 | 8/2012 | Bonutti |
| 2012/0226198 | A1 | 9/2012 | Carson |
| 2012/0226481 | A1 | 9/2012 | Carson |
| 2012/0245699 | A1 | 9/2012 | Lang et al. |
| 2012/0310617 | A1 | 12/2012 | Bellettre et al. |
| 2013/0103363 | A1 | 4/2013 | Lang et al. |
| 2013/0110471 | A1 | 5/2013 | Lang et al. |
| 2013/0211531 | A1 | 8/2013 | Steines et al. |
| 2013/0226185 | A1 | 8/2013 | Bonutti |
| 2013/0237989 | A1 | 9/2013 | Bonutti |
| 2013/0238039 | A1 | 9/2013 | Bonutti |
| 2013/0245803 | A1 | 9/2013 | Lang |
| 2013/0289729 | A1 | 10/2013 | Bonutti |
| 2014/0005792 | A1 | 1/2014 | Lang et al. |
| 2014/0031826 | A1 | 1/2014 | Bojarski et al. |
| 2014/0066959 | A1 | 3/2014 | Bonutti |
| 2014/0142710 | A1 | 5/2014 | Lang |
| 2014/0188134 | A1 | 7/2014 | Nortman et al. |
| 2014/0188240 | A1 | 7/2014 | Lang et al. |
| 2014/0194989 | A1 | 7/2014 | Bonutti |
| 2014/0200621 | A1 | 7/2014 | Malackowski et al. |
| 2014/0228860 | A1 | 8/2014 | Steines et al. |
| 2014/0309560 | A1 | 10/2014 | Bonutti |
| 2014/0330278 | A1 | 11/2014 | Park et al. |
| 2014/0330279 | A1 | 11/2014 | Park et al. |
| 2015/0032217 | A1 | 1/2015 | Bojarski et al. |
| 2015/0250597 | A1 | 9/2015 | Lang et al. |
| 2015/0257768 | A1 | 9/2015 | Bonutti |
| 2015/0320500 | A1 | 11/2015 | Lightcap et al. |
| 2015/0335444 | A1 | 11/2015 | Caballes |
| 2016/0015466 | A1 | 1/2016 | Park et al. |
| 2016/0030126 | A1 | 2/2016 | Netravali et al. |
| 2016/0038243 | A1 | 2/2016 | Miller et al. |
| 2016/0038244 | A1 | 2/2016 | Netravali et al. |
| 2016/0038291 | A1 | 2/2016 | Netravali et al. |
| 2016/0074124 | A1 | 3/2016 | Fitz et al. |
| 2016/0081758 | A1 | 3/2016 | Bonutti |
| 2016/0095609 | A1 | 4/2016 | Park et al. |
| 2016/0143744 | A1 | 5/2016 | Bojarski et al. |
| 2016/0143749 | A1 | 5/2016 | Holovacs et al. |
| 2016/0175054 | A1 | 6/2016 | Kang et al. |
| 2016/0199136 | A1 | 7/2016 | Iorgulescu et al. |
| 2016/0206331 | A1 | 7/2016 | Fitz et al. |
| 2016/0206375 | A1 | 7/2016 | Abbasi et al. |
| 2016/0206377 | A1 | 7/2016 | Cheal et al. |
| 2016/0228193 | A1 | 8/2016 | Moctezuma de la Barrera et al. |
| 2016/0228204 | A1 | 8/2016 | Quaid et al. |
| 2016/0242931 | A1 | 8/2016 | Wong et al. |
| 2016/0262910 | A1 | 9/2016 | Axelson, Jr. et al. |
| 2016/0270854 | A1 | 9/2016 | Chaoui |
| 2016/0310282 | A1 | 10/2016 | Bojarski et al. |
| 2016/0317312 | A1 | 11/2016 | Bojarski et al. |
| 2016/0324581 | A1 | 11/2016 | Bojarski et al. |
| 2016/0324648 | A1 | 11/2016 | Hodorek et al. |
| 2016/0331467 | A1 | 11/2016 | Slamin et al. |
| 2016/0331481 | A1 | 11/2016 | Bonutti |

(56)                    References Cited

U.S. PATENT DOCUMENTS

| | | | |
|---|---|---|---|
| 2016/0374693 | A1 | 12/2016 | Van Citters et al. |
| 2017/0000562 | A1 | 1/2017 | Frank et al. |
| 2017/0007275 | A1 | 1/2017 | Park et al. |
| 2017/0007331 | A1 | 1/2017 | Couture et al. |
| 2017/0007408 | A1 | 1/2017 | Fitz et al. |
| 2017/0020613 | A1 | 1/2017 | Kang et al. |
| 2017/0049487 | A1 | 2/2017 | Bonutti et al. |
| 2017/0056022 | A1 | 3/2017 | Cheal et al. |
| 2017/0056183 | A1 | 3/2017 | Steines et al. |
| 2017/0065347 | A1 | 3/2017 | Bojarski et al. |
| 2017/0119531 | A1 | 5/2017 | Bojarski et al. |
| 2017/0151021 | A1 | 6/2017 | Quaid, III |
| 2017/0164957 | A1 | 6/2017 | Bojarski et al. |
| 2017/0172665 | A1 | 6/2017 | Otto et al. |
| 2017/0181755 | A1* | 6/2017 | Librot ..................... A61B 34/20 |
| 2017/0181798 | A1 | 6/2017 | Panescu et al. |
| 2017/0189203 | A1 | 7/2017 | Hagag et al. |
| 2017/0231771 | A1* | 8/2017 | Piron ................... A61B 8/0841 |
| | | | 606/102 |
| 2017/0360456 | A1 | 12/2017 | Gunther |
| 2018/0271667 | A1 | 9/2018 | Kemp et al. |
| 2019/0133791 | A1 | 5/2019 | Yadav et al. |

FOREIGN PATENT DOCUMENTS

| | | | |
|---|---|---|---|
| WO | 2010068213 | A1 | 6/2010 |
| WO | 2016094298 | A1 | 6/2016 |
| WO | 2016115306 | A1 | 7/2016 |
| WO | 2016115423 | A1 | 7/2016 |
| WO | 2017004056 | A1 | 1/2017 |

OTHER PUBLICATIONS

Arthrex, Inc., "Patient's Guide to Shoulder Replacement Surgery with the Arthrex Eclipse and Univers II Brochure", 2015, 12 pages.
Atmani, H. et al., "Computer-Aided Surgery System for Shoulder Prosthesis Placement", Computer Aided Surgery, vol. 12, No. 1, Jan. 2007, pp. 60-70.

Biomet Orthopedics, "Comprehensive Nano Stemless Shoulder Anatomic and Reverse Brochure", 2012, 60 pages.
Biomet Orthopedics, "T.E.S.S. Shoulder System Surgical Technique Brochure", 2011, 43 pages.
Casagrande MD, Danielle J. et al., "Radiographic Evaluation of Short-Stem Press-Fit Total Shoulder Arthroplasty: Short-Term Follow-Up", Journal of Shoulder and Elbow Surgery, vol. 25, Issue 7, Jul. 2016, pp. 1163-1169.
Choi et al., "Visbone: 3D Visualization of Bone Mineral Density", Pacific Conference on Computer Graphics and Applications, IEEE Computer Society, 1999, pp. 138-146.
Costouros, MD FACS, John G., "Stemless Shoulder Arthroplasty Presentation", 2017, 41 pages.
FX Solutions, "Easytech Anatomical Surgical Technique Brochure", 2016, 8 pages.
Harmer, L. et al., "Total Shoulder Arthroplasty: Are the Humeral Components Getting Shorter?", Curr. Rev. Muscuskelet. Med., vol. 9, Issue 1, Mar. 2016, pp. 17-22.
Lima Corporate, "SMR System Surgical Technique Brochure", 2015, 62 pages.
Mathys European Orthopaedics, Affinis Short—Short Stemmed Total Shoulder Prosthesis Brochure, 2016, 28 pages.
Nguyen, Duong et al., "Improved Accuracy of Computer-Assisted Glenoid Implantation in Total Shoulder Arthroplasty: An In-Vitro Randomized Controlled Trial", Journal of Shoulder and Elbow Surgery, vol. 18, 2009, pp. 907-914.
Pandey, Rupesh Kumar et al., "Drilling of Bone: A Comprehensive Review", Journal of Orthopaedics and Trauma, vol. 4, 2013, pp. 15-30.
Schnetzke, M. et al., "Radiologic Bone Adaptations on a Cementless Short-Stem Shoulder Prosthesis", J. Shoulder Elbow Surg., vol. 25, Issue 4, Apr. 2016, pp. 650-657.
Stryker, "Reunion TSA—Total Shoulder Arthroplasty System-Operative Technique", Sep. 2016, pp. 1-88.
Wright, "Tomier Simpliciti Shoulder System Surgical Technique Brochure", 2016, 24 pages.
Zimmer Biomet, "Sidus Stem-Free Shoulder Brochure", Jan. 2018, 40 pages.

* cited by examiner

ROBOTIC SYSTEM FOR SHOULDER ARTHROPLASTY USING STEMLESS IMPLANT COMPONENTS

RELATED APPLICATIONS

This application is a Continuation of U.S. patent application Ser. No. 16/181,766, filed on Nov. 6, 2018, and issued as U.S. Pat. No. 11,173,048 on Nov. 16, 2021, which claims priority to and the benefit of U.S. Provisional Patent Application No. 62/582,624, filed on Nov. 7, 2017, the disclosures of each of which are hereby incorporated by reference in their entirety.

TECHNICAL FIELD

The present disclosure relates generally to robotic systems and, more particularly, to robotic systems for shoulder arthroplasty.

BACKGROUND

Robotic systems used in surgery are well known. One such system comprises a robotic manipulator and a cutting tool for sculpting a bone into a desired shape. The cutting tool is coupled to the robotic manipulator to remove material from the bone for purposes of creating space to receive an implant. Typically, these systems are used to prepare bones for hip implants and knee implants. As the world population continues to live longer, there is a growing need for arthroplasty. Owing to the relatively greater need for hip arthroplasty and knee arthroplasty, prior art robotic systems focus on preparing bones for hip and knee procedures. There remains a need for robotic systems for shoulder arthroplasty to provide higher accuracy and more precision in replacing shoulder joints.

Shoulder arthroplasty procedures commonly involve preparing a patient's humerus to receive a stemmed implant and preparing the patient's glenoid cavity to receive a glenoid implant. However, in some cases, instead of preparing the humerus to receive a stemmed implant, the humerus is prepared for a stemless implant. Generally speaking, stemless implants are bone-sparing, meaning that less bony material is required to be removed from the patient as compared to stemmed implants. This can provide several advantages to the patient. Yet, because a stem is not placed in the humerus, i.e., in a humeral canal that can enhance stability of the implant, there is a desire and need for stemless implants and procedures that securely place such stemless implants in the humerus.

SUMMARY

A robotic surgery system is provided for preparing a bone of a shoulder joint to receive a shoulder implant. The shoulder implant has a proximal body defining a center axis and an eccentric distal projection. The robotic surgery system comprises a robotic manipulator and a cutting tool to be coupled to the robotic manipulator. A localizer is configured to track movement of the cutting tool and the bone. A controller is coupled to the robotic manipulator and the localizer. The controller is configured to operate the robotic manipulator to control movement of the cutting tool relative to the bone based on a virtual object associated with the shoulder implant, wherein the virtual object defines a volume of material to be removed from the bone to receive the eccentric distal projection. The virtual object is defined in a coordinate system at a location based on density data of the bone such that, when the shoulder implant is fully seated in the bone, the eccentric distal projection is located in a first region of the bone having a density characteristic greater than an adjacent second region of the bone.

A method is also provided for performing robotic surgery with a robotic manipulator and a cutting tool coupled to the robotic manipulator to prepare a bone of a shoulder joint to receive a shoulder implant. The shoulder implant has a proximal body defining a center axis and an eccentric distal projection. The method comprises registering a coordinate system to the bone, tracking movement of the cutting tool, and tracking movement of the bone. The method also comprises controlling movement of the cutting tool relative to the bone based on a virtual object associated with the shoulder implant, wherein the virtual object defines a volume of material to be removed from the bone to receive the eccentric distal projection. A location of the virtual object in the coordinate system is determined based on density data of the bone such that, when the shoulder implant is fully seated in the bone, the eccentric distal projection is located in a first region of the bone having a density characteristic greater than an adjacent second region of the bone.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
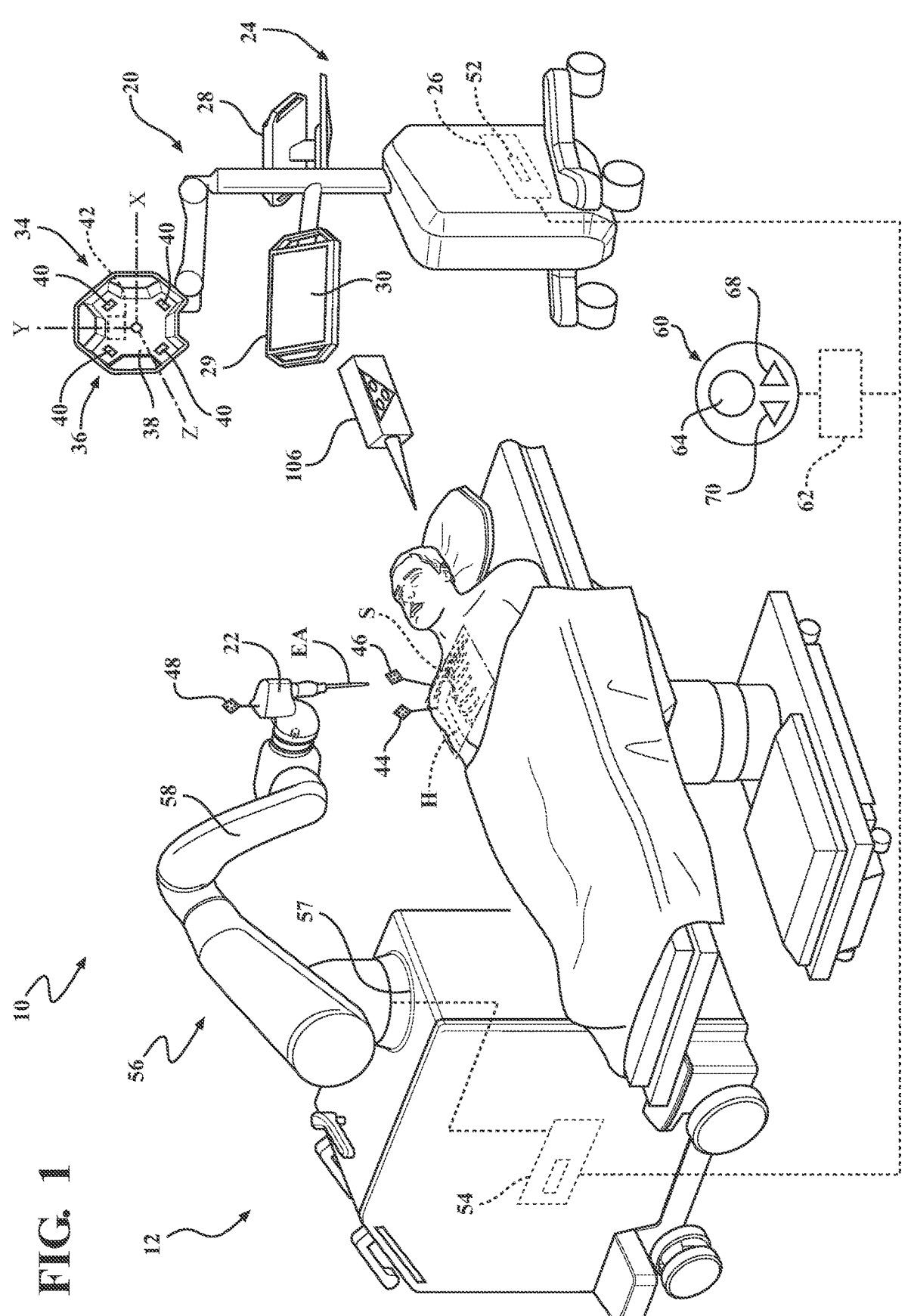
FIG. 1 is a perspective view of a robotic system for shoulder arthroplasty.

Referring to FIG. 1, a robotic system 10 is illustrated for performing surgery on a patient. The version shown in FIG.

1 comprises a material removal system for removing material from a workpiece (e.g., bone), but it should be appreciated that other types of robotic systems are also contemplated. The robotic system 10 is shown in a surgical setting such as an operating room of a medical facility. In the embodiment shown, the robotic system 10 includes a machining station 12 and a guidance station 20.

The guidance station 20 is set up to track movement of various objects in the operating room. Such objects include, for example, a surgical tool 22, a humerus H of a patient, and a scapula S of the patient. The guidance station 20 tracks these objects for purposes of displaying their relative positions and orientations to the surgeon and, in some cases, for purposes of controlling movement (e.g., causing movement, guiding movement, constraining movement, etc.) of the surgical tool 22 relative to virtual cutting boundaries or other virtual objects associated with the humerus H and scapula S.

The guidance station 20 includes a computer cart assembly 24 that houses a navigation controller 26. A navigation interface is in operative communication with the navigation controller 26. The navigation interface includes a first display 28 adapted to be situated outside of a sterile field and a second display 29 adapted to be situated inside the sterile field. The displays 28, 29 are adjustably mounted to the computer cart assembly 24. First and second input devices such as a keyboard and mouse can be used to input information into the navigation controller 26 or otherwise select/control certain aspects of the navigation controller 26. Other input devices are contemplated including a touch screen 30 or voice-activation.

A localizer 34 communicates with the navigation controller 26. In the embodiment shown, the localizer 34 is an optical localizer and includes a camera unit 36. Other types of localizers are also contemplated, including localizers that employ ultrasound, radio frequency (RF) signals, electromagnetic fields, and the like. The camera unit 36 has an outer casing 38 that houses one or more optical position sensors 40. In some embodiments at least two optical sensors 40 are employed, preferably three or four. The optical sensors 40 may be four separate charge-coupled devices (CCD). In one embodiment four, one-dimensional CCDs are employed. It should be appreciated that in other embodiments, separate camera units, each with a separate CCD, or two or more CCDs, could also be arranged around the operating room. The CCDs detect infrared (IR) signals.

The camera unit 36 is mounted on an adjustable arm to position the optical sensors 40 with a field of view of the below discussed trackers that, ideally, is free from obstructions. In some embodiments the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation controller 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation controller 26.

Position and orientation signals and/or data are transmitted to the navigation controller 26 for purposes of tracking objects. The computer cart assembly 24, display 28, and camera unit 36 may be like those described in U.S. Pat. No.

7,725,162 to Malackowski, et al. issued on May 25, 2010, entitled "Surgery System," hereby incorporated by reference.

The navigation controller 26 can be a personal computer or laptop computer. The navigation controller 26 has the display 28, central processing unit (CPU) and/or other processors, memory (not shown), and storage (not shown). The navigation controller 26 is loaded with software. The software converts the signals received from the camera unit 36 into data representative of the position and orientation of the objects being tracked.

The guidance station 20 is operable with a plurality of tracking devices 44, 46, 48, also referred to herein as trackers. In the illustrated embodiment, one tracker 44 is firmly affixed to the humerus H of the patient and another tracker 46 is firmly affixed to the scapula S of the patient. The trackers 44, 46 are firmly affixed to sections of bone. The trackers 44, 46 could be mounted like those shown in U.S. Patent Application Publication No. 2014/0200621, published on Jul. 17, 2014, entitled, "Navigation Systems and Methods for Indicating and Reducing Line-of-Sight Errors," the entire disclosure of which is hereby incorporated by reference. The trackers 44, 46 could be mounted to other tissue types or parts of the anatomy.

A tool tracker 48 is firmly attached to the surgical tool 22. The tool tracker 48 may be integrated into the surgical tool 22 during manufacture or may be separately mounted to the surgical tool 22 in preparation for surgical procedures. In the embodiment shown, the surgical tool 22 is attached to a manipulator 56 of the machining station 12. Such an arrangement is shown in U.S. Pat. No. 9,119,655, issued Sep. 1, 2015, entitled, "Surgical Manipulator Capable of Controlling a Surgical Instrument in Multiple Modes," the entire disclosure of which is hereby incorporated by reference.

A separate tracker (not shown) may be attached to a base 57 of the manipulator 56 to track movement of the base 57 in some embodiments. In this case, the working end of the surgical tool 22 may be tracked via the base tracker by virtue of additional encoder data being provided by encoders in joints of the manipulator 56, which provide joint position data that can be collectively processed to generate information regarding a location of the working end of the surgical tool 22 relative to the base 57. The working end of the surgical tool 22, which is being tracked by virtue of the tool tracker 48 (or base tracker in some cases), may be an energy applicator EA such as a rotating bur, saw blade, electrical ablation device, or the like. The energy applicator EA may be a separate component that is releasably connected to a handpiece of the surgical tool 22 or may be integrally formed with the handpiece.

The trackers 44, 46, 48 can be battery powered with an internal battery or may have leads to receive power through the navigation controller 26, which, like the camera unit 36, receives external power.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 (see FIG. 2) transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs (not shown). In some embodiments, the light signals from the LEDs 50 are fired at different rates for each tracker 44, 46, 48.

Each of the LEDs 50 are connected to a tracker controller (not shown) located in a housing of the associated tracker 44, 46, 48 that transmits/receives data to/from the navigation controller 26. In one embodiment, the tracker controllers transmit data on the order of several Megabytes/second through wired connections with the navigation controller 26. In other embodiments, a wireless connection may be used. In these embodiments, the navigation controller 26 has a transceiver (not shown) to receive the data from the tracker controller.

In other embodiments, the trackers 44, 46, 48 may have passive markers (not shown), such as reflectors that reflect light emitted from the camera unit 36. The reflected light is then received by the optical sensors 40. Active and passive arrangements are well known in the art.

In some embodiments, the trackers 44, 46, 48 also include a gyroscope sensor and accelerometer, such as the trackers shown in U.S. Pat. No. 9,008,757, issued on Apr. 14, 2015, entitled, "Navigation System Including Optical and Non-Optical Sensors," the entire disclosure of which is hereby incorporated by reference.

The navigation controller 26 includes a navigation processor 52. It should be understood that the navigation processor 52 could include one or more processors to control operation of the navigation controller 26. The processors can be any type of microprocessor or multi-processor system. The navigation controller 26 may additionally or alternatively comprise one or more microcontrollers, field programmable gate arrays, systems on a chip, discrete circuitry, and/or other suitable hardware, software, or firmware that is capable of carrying out the functions described herein. The term processor is not intended to limit the scope of any embodiment to a single processor.

The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some embodiments), navigation processor 52 generates data indicating the relative positions and orientations of the trackers 44, 46, 48 relative to the localizer 34 using triangulation and/or other techniques.

Prior to the start of the surgical procedure, additional data are loaded into the navigation processor 52. Based on the position and orientation of the trackers 44, 46, 48 and the previously loaded data, the navigation processor 52 determines the position of the working end of the surgical tool 22 (e.g., the centroid of a surgical bur, cutting envelope of a sagittal saw, etc.) and the orientation of the surgical tool 22 relative to the tissue against which the working end is to be applied. In some embodiments, the navigation processor 52 forwards these data to a manipulator controller 54. The manipulator controller 54 can then use the data to control the manipulator 56 as described in U.S. Pat. No. 9,119,655, issued Sep. 1, 2015, entitled, "Surgical Manipulator Capable of Controlling a Surgical Instrument in Multiple Modes," the entire disclosure of which is hereby incorporated by reference.

In one embodiment, the surgical tool 22 is controlled to stay within one or more preoperatively defined virtual boundaries set by the surgeon, which defines the material (e.g., tissue) of the humerus H and scapula S to be removed by the surgical tool 22. These boundaries are defined by virtual objects stored in memory in the robotic system 10 (e.g., in the navigation controller 26 and/or the manipulator controller 54). The boundaries may be defined within a virtual model of the humerus H and scapula S and be represented as a mesh surface, constructive solid geometry (CSG), voxels, or may be represented using other boundary representation techniques. The boundaries may also be defined separately from virtual models of the humerus H and scapula S.

The navigation processor 52 also generates image signals that indicate the relative position of the working end of the surgical tool 22 to the tissue to be removed. These image signals are applied to the displays 28, 29. The displays 28, 29, based on these signals, generate images that allow the surgeon and staff to view the relative position of the working end to the surgical site. The displays, 28, 29, as discussed above, may include a touch screen or other input/output device that allows entry of commands.

In the embodiment shown in FIG. 1, the surgical tool 22 forms part of an end effector of the manipulator 56. The manipulator 56 has a plurality of links 58 extending from the base 57, and a plurality of active joints (not numbered) for moving the surgical tool 22 with respect to the base 57. The links 58 may form a serial robotic arm structure as shown, a parallel robotic arm structure (not shown), or other suitable structure.

The manipulator 56 has the ability to operate in one or more of: (1) a free mode in which a user grasps the end effector of the manipulator 56 in order to cause movement of the surgical tool 22 (e.g., directly, through force/torque sensor measurements that cause active driving of the manipulator 56, passively, or otherwise); (2) a haptic mode in which the user grasps the end effector of the manipulator 56 to cause movement as in the free mode, but is restricted in movement by the virtual boundaries defined by the virtual objects stored in the robotic system 10; (3) a semi-autonomous mode in which the surgical tool 22 is moved by the manipulator 56 along a tool path (e.g., the active joints of the manipulator 56 are operated to move the surgical tool 22 without requiring force/torque on the end effector from the user); (4) a service mode in which the manipulator 56 performs preprogrammed automated movements to enable servicing; or (5) other modes to facilitate preparation of the manipulator 56 for use, e.g., for draping, etc. Examples of operation in the haptic mode and the semi-autonomous mode are described in U.S. Pat. No. 8,010,180, issued Aug. 30, 2011, entitled, "Haptic Guidance System and Method" and U.S. Pat. No. 9,119,655, issued Sep. 1, 2015, entitled, "Surgical Manipulator Capable of Controlling a Surgical Instrument in Multiple Modes," the entire disclosures of both of which are hereby incorporated by reference.

During operation in the haptic mode, for certain surgical tasks, the user manually manipulates (e.g., manually moves or manually causes the movement of) the manipulator 56 to manipulate the surgical tool 22 to perform the surgical procedure on the patient, such as drilling, cutting, reaming, implant installation, and the like. As the user manipulates the surgical tool 22, the guidance station 20 tracks the location of the surgical tool 22 and/or the manipulator 56 and provides haptic feedback (e.g., force feedback) to the user to limit the user's ability to manually move (or manually cause movement of) the surgical tool 22 beyond one or more predefined virtual boundaries that are registered (mapped) to the patient's anatomy, which results in highly accurate and repeatable drilling, cutting, reaming, and/or implant placement.

The manipulator controller 54 may have a central processing unit (CPU) and/or other manipulator processors, memory (not shown), and storage (not shown). The manipulator controller 54 is loaded with software as described below. The manipulator processors could include one or more processors to control operation of the manipulator 56. The processors can be any type of microprocessor, multiprocessor, and/or multi-core processing system. The manipulator controller 54 may additionally or alternatively comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

In one version, in the haptic mode, the manipulator controller 54 determines the desired location to which the surgical tool 22 should be moved based on forces and torques applied by the user on the surgical tool 22. In this version, most users are physically unable to actually move the manipulator 56 any appreciable amount to reach the desired position, but the manipulator 56 emulates the user's desired positioning by sensing the applied forces and torques and reacting in a way that gives the user the impression that the user is actually moving the surgical tool 22 even though active motors on the joints are performing the movement. For example, based on the determination of the desired location to which the user wishes to move, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers (not shown) (e.g., one for controlling each motor) that control the active joints of the manipulator 56 to move the plurality of links 58 and thereby move the surgical tool 22 from the current location to the desired location.

A user control pendant assembly 60 may be used to interface with the manipulator controller 54 in the semi-autonomous mode and/or to switch between the free mode, haptic mode, semi-autonomous mode, service mode, and/or other modes. The user control pendant assembly 60 includes a processor or pendant controller 62. The pendant controller 62 may have a central processing unit (CPU) and/or other pendant processors, memory (not shown), and storage (not shown). The pendant controller 62 is in communication with the manipulator controller 54. The pendant controller 62 is also in communication with switches (not shown) associated with user controls such as buttons 64, 68, 70. The pendant processor could include one or more processors to transmit signals resulting from pressing of buttons 64, 68, 70 on the user control pendant assembly 60 to the manipulator controller 54. Once the practitioner is ready to begin autonomous advancement of the surgical tool 22, in the semi-autonomous mode, for example, the practitioner depresses button 64 (and may be required to hold down button 64 to continue autonomous operation). In some versions, based on the depression of buttons 68 and 70, a feed rate (e.g., velocity) of the working end of the surgical tool 22 may be controlled.

Figure 3:
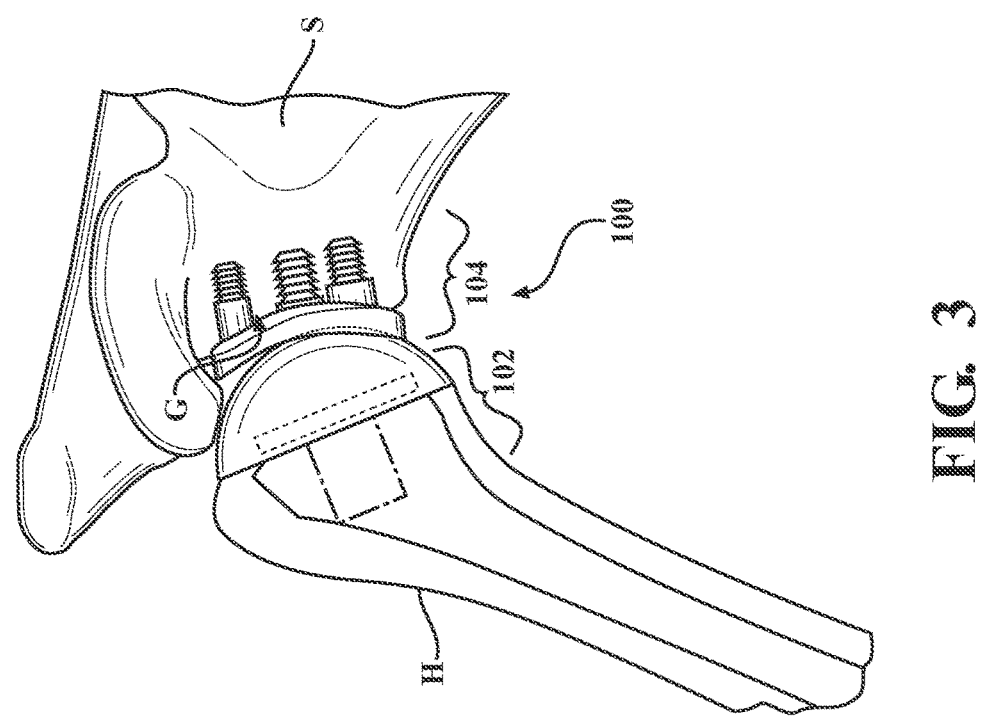
FIG. 3 is an illustration of a shoulder implant system replacing the natural shoulder joint.
Figure 2:
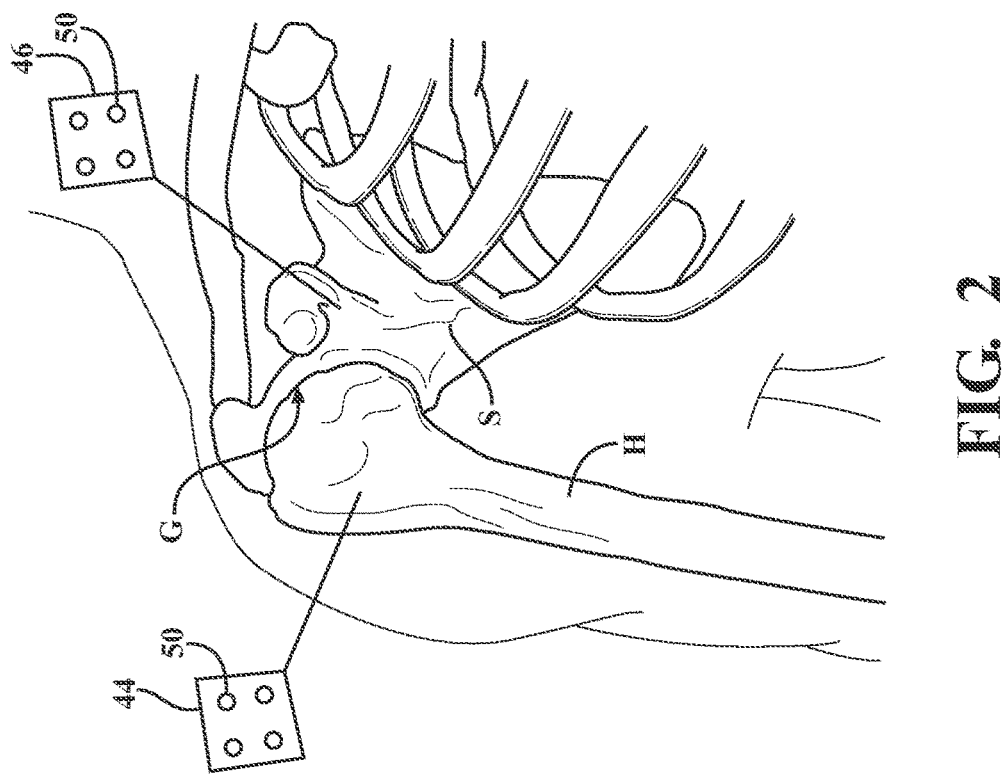
FIG. 2 is an illustration of a shoulder joint requiring arthroplasty.

Referring to FIGS. 2 and 3, pre-operative imaging and/or intra-operative imaging may be employed to visualize the patient's anatomy that requires treatment—such as the patient's shoulder joint. The surgeon plans where to place a shoulder implant system 100 with respect to the images and/or with respect to one or more 3-D models created from the images, such as 3-D models of the humerus H and the scapula S created from CT scan data, MRI data, or the like. Such models may also be based on generic bone models morphed to resemble patient specific anatomy. Planning includes determining a pose of each implant component of the shoulder implant system 100 with respect to the particular bone in which they are being placed, e.g., by identifying the desired pose of the implant component in the images and/or the appropriate 3-D model. This may include creating or positioning a separate 3-D model of the implant components with respect to the 3-D models of the patient's anatomy. Once the plan is set, then the plan is transferred to the robotic system 10 for execution. The 3-D models may comprise mesh surfaces, constructive solid geometries (CSG), voxels, or may be represented using other 3-D modeling techniques.

The robotic system 10 may be employed to prepare the humerus H and a glenoid cavity G of a scapula S to receive the shoulder implant system 100. In this case, the shoulder implant system 100 comprises a humeral component 102 and a glenoid component 104. The humerus H is prepared by the robotic system 10 to receive the humeral component 102, which in some embodiments is stemless and the glenoid cavity G is prepared by the robotic system 10 to receive the glenoid component 104.

Virtual boundaries, pre-defined tool paths, and/or other autonomous movement instructions, that correspond to the desired placement of the humeral component 102 and the glenoid component 104 are created to control movement of the manipulator 56 so that the working end of the surgical tool 22 (e.g., bur, drill, saw) are controlled in a manner that ultimately places the components 102, 104 according to the user's plan. This may comprise ensuring during the surgical procedure that the surgical tool 22 (or cutting accessory attached to it) stays within a pre-defined cutting volume delineating the bounds of the material to be removed to receive the implant. This may also comprise, for example, ensuring during the surgical procedure that a trajectory of the surgical tool 22 is aligned with a desired pose of peg holes, that the trajectory of the surgical tool 22 is aligned with a desired pose of pilot holes for anchoring screws, and the like. This may further comprise ensuring that a plane of the surgical tool 22 (e.g., for a sagittal saw) is aligned with a desired pose of a planar resection.

The robotic system 10 and/or the user may pre-operatively plan the desired cutting volume, trajectories, planar cuts, etc. For example, the desired cutting volumes may simply correspond to the geometry of the implants being used. Furthermore, these cutting volumes may be virtually located and registered to the anatomy by virtue of the user planning the location of the implants relative to the 3-D models of the humerus H and scapula S and registering the 3-D models of the implants, along with the 3-D models of the humerus H and the scapula S to the actual humerus H and scapula S during the procedure.

The robotic system 10 and/or the user may also intra-operatively plan the desired cutting volume, trajectories, planar cuts, etc. or may intra-operatively adjust the cutting volumes, trajectories, planar cuts, etc. that were defined pre-operatively. For example, in the free mode, the user could position a drill or bur at a desired entry point relative to the anatomy of interest, e.g., the humerus, and orient the drill or bur until the display 28, 29 shows that the trajectory of a rotational axis of the drill or bur is in a desired orientation. Once the user is satisfied with the trajectory, the user provides input to the robotic system 10 to set this trajectory as the desired trajectory to be maintained during the procedure. The input could be provided via input devices such as the mouse, keyboard, touchscreen, push button, foot pedal, etc. coupled to the navigation controller 26 or the manipulator controller 54. This same procedure can be followed for the user to set a desired planar cut, etc. 3-D models of the cutting volumes, desired trajectory, desired planar cuts, etc. are stored in memory for retrieval during the procedure.

One or more boundaries used by the robotic system 10 could be defined by a navigation pointer 106 by touching anatomy of interest with the navigation pointer 106 and capturing associated points on the anatomy with the guidance station 20. For example, the navigation pointer 106 (FIGS. 1 and 4) could be used to outline the boundary. Additionally, or alternatively, the navigation pointer 106 could be used to delineate soft tissue or other sensitive anatomical structures to be avoided by the surgical tool 22. These points, for example, could be loaded into the robotic system 10 to adjust the tool path to be followed in the semi-autonomous mode so that the surgical tool 22 avoids these areas. Other methods could be used to delineate and/or define anatomy of interest, e.g., as being anatomy to be removed, anatomy to be avoided, etc.

A line haptic object LH (see briefly FIG. 7) may be created and stored in the robotic system 10 to constrain movement of the surgical tool 22 to stay along the desired trajectory. The line haptic object LH may have a starting point SP, as described further below and a target point TP, which defines a desired depth of the drill. A planar haptic object PH (see FIG. 5) may be created for constraining movement of the surgical tool 22 to stay along a desired plane. Other haptic object shapes, sizes, etc. are also contemplated, including those that define volumes of material to be removed to receive the components 102, 104, as described further below. It should also be appreciated that other forms of virtual objects, other than haptic objects, could be employed to establish boundaries for the surgical tool 22, wherein such boundaries may be represented on one or more of the displays 28, 29 to show the user when the working end of the surgical tool 22 is approaching, reaching, and/or exceeding such boundaries.

Figures 4, 5:
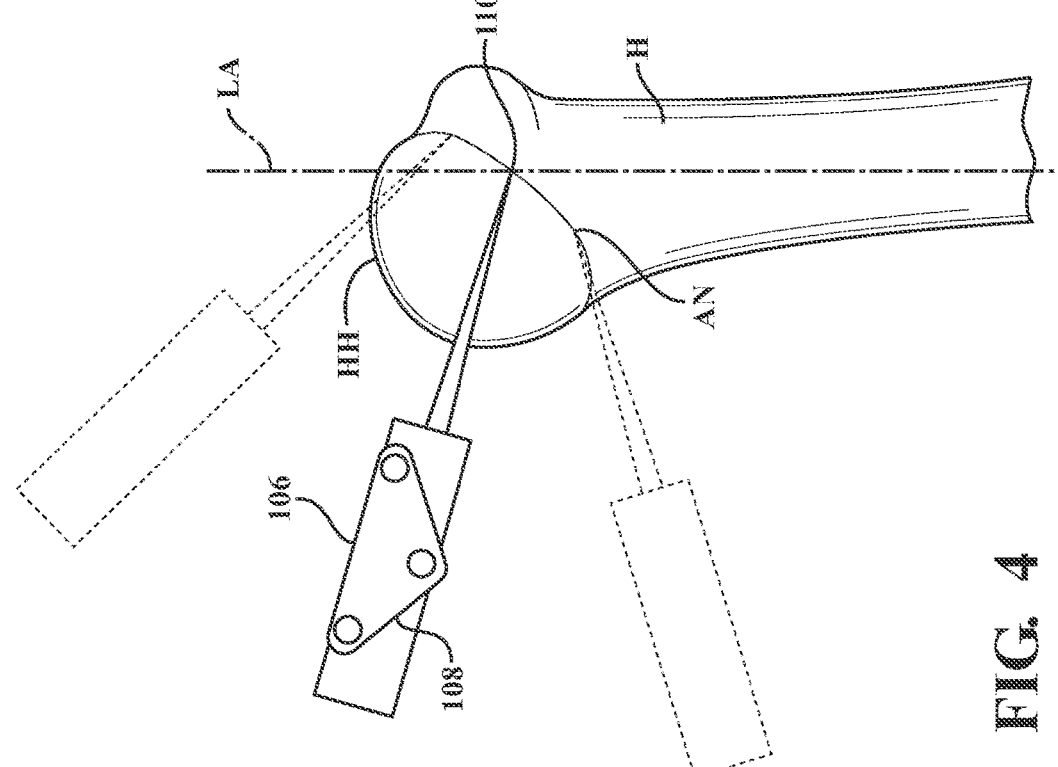
FIG. 4 is an illustration of a navigation pointer being used to locate landmarks on a humerus.
FIG. 5 is an illustration of a virtual object defining a resection plane for a humeral head of the humerus.

Referring to FIGS. 4 and 5, the humerus H is shown. The description that follows relates to preparation of the humerus H to receive the humeral component 102, but it should be appreciated that, during a surgical procedure, either of the humerus H or the glenoid cavity G may be prepared first to receive its associated implant component, or some combination of alternating preparation could be employed. The humerus H is prepared by first defining a resection plane along which a humeral head HH is to be resected from a remaining portion of the humerus H. This resection is planar in some embodiments, but may comprise a more complex surface topology in other embodiments. For example, the resection could provide a contoured surface, an undulating surface of ridges, or the like.

One of several options may be employed to determine the location of the resection of the humeral head HH, and by extension the location of the planar haptic object PH. In one case, a surgeon may prefer to make the resection along an anatomical neck AN. In this case, referring to FIG. 4, the surgeon may establish a virtual resection plane for the resection by using the navigation pointer 106, which comprises its own tracker 108 for purposes of determining a location of its tip 110. Navigation pointers 106 are used in registering pre-operative images or models to actual anatomy being treated during a surgical procedure. Here, the navigation pointer 106 may be used to register a pre-operative 3-D model (e.g., one generated from CT scan data, MRI data, or the like) of the humerus H to the actual humerus H and also to define the resection of the humeral head HH.

In order to define the resection of the humeral head HH, the user touches the tip 110 of the navigation pointer 106 to at least three locations along the anatomical neck AN, and the navigation controller 26 determines positions of these plurality of landmarks in a coordinate system registered to the humerus H (one or more coordinate systems may be employed). Once the positions of the landmarks are determined, the virtual resection plane can be defined as passing through each of the three points in the coordinate system. The location of the virtual resection plane defines a location of the planar haptic object PH shown in FIG. 5.

Other methods of establishing the resection includes placing the resection plane at a predetermined angle (e.g., 135 degrees or other angle) with respect to a longitudinal axis LA of the humerus (e.g. relative to an intramedullary axis of the intramedullary canal) defined in the coordinate system. Yet another method of establishing the plane comprises selecting one or more landmarks on the humerus H, e.g., the greater tuberosity, lesser tuberosity, bicipital groove, and defining the resection based on the one or more landmarks, either alone, or in conjunction with the intramedullary axis of the intramedullary canal and/or in conjunction with an extramedullary axis or axis based on an outer shape of the humerus H.

Once the resection location has been determined, the robotic system 10 creates the virtual object required to guide operation of the manipulator 56 and the surgical tool 22 and stores the virtual object in memory. As shown in FIG. 5, the surgical tool 22 comprises a sagittal saw blade 112. The virtual object, in this case the planar haptic object PH, is employed to constrain movement of the saw blade 112 so that the resection is made according to the surgeon's plan. This may include operating the manipulator 56 in the haptic mode and/or semi-autonomous mode to perform the resection. In the haptic mode, the user manually manipulates the surgical tool 22 while the manipulator 56 keeps the saw blade 112 confined within the planar haptic object PH via haptic feedback to the user.

Visual feedback can additionally be provided on the displays 28, 29, which depict a representation of the saw blade 112 and a representation of the humerus H and updates in substantially real-time such representations so that the user and/or others can visualize movement of the saw blade 112 relative to the humerus H during resection. The user operates the saw blade 112 to finish the resection and ready the humerus H for further preparation to receive the humeral component 102. In some versions, the humeral head HH is manually resected using a conventional sagittal saw outfitted with a separate navigation tracker so that the user can visualize a location of the saw blade 112 relative to the desired resection on the displays 28, 29 while manually resecting the humeral head HH.

In some embodiments, before sawing commences, the robotic system 10 autonomously aligns the saw blade 112 with the desired resection plane. Such autonomous positioning may be initiated by the user pulling a trigger (not shown) on the surgical tool 22, or otherwise providing input to the robotic system 10 to start the autonomous movement. In some cases, a reference point RP of the surgical tool 22 is first brought to within a predefined distance of a starting point SP of the planar haptic object PH (such as within a predefined starting sphere as shown or starting box). Once the reference point RP is within the predefined distance of the starting point SP, then pulling the trigger (or alternatively pressing a foot pedal or actuating some other input) causes the manipulator 56 to autonomously align and position the saw blade 112 on the desired plane. Once the saw blade 112 is in the desired pose, the robotic system 10 may effectively hold the surgical tool 22 on the desired plane (i.e., within the planar haptic object PH) by tracking movement of the patient and autonomously adjusting the manipulator 56 as needed to keep the saw blade 112 on the desired trajectory/plane.

While the robotic system 10 holds the saw blade 112 on the desired plane, the user may then manually manipulate the surgical tool 22 to move (or cause movement of) the saw blade 112 within the planar haptic object PH toward the bone to resect the humeral head HH. In some cases, such as in the haptic mode, the robotic system 10 constrains the user's movement of the surgical tool 22 to stay in the planar haptic object PH by providing haptic feedback to the user should the user attempt to move the surgical tool 22 in a manner that deviates from the planar haptic object PH and the desired plane. If the user desires to return the manipulator 56 to a free mode, for unconstrained movement of the surgical tool 22, the user can then pull the surgical tool 22 back along the planar haptic object PH, away from the patient, until an exit point of the planar haptic object PH is reached.

Figure 8:
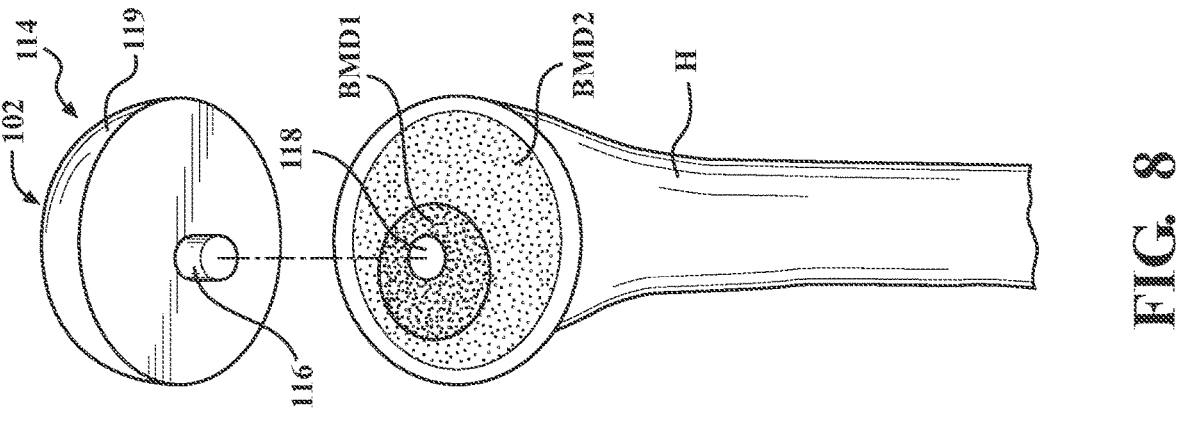
FIG. 8 is a top perspective view of the humerus of FIG. 7 after material has been removed from a volume of tissue having a relatively higher density to receive an eccentric humeral head component.
Figure 7:
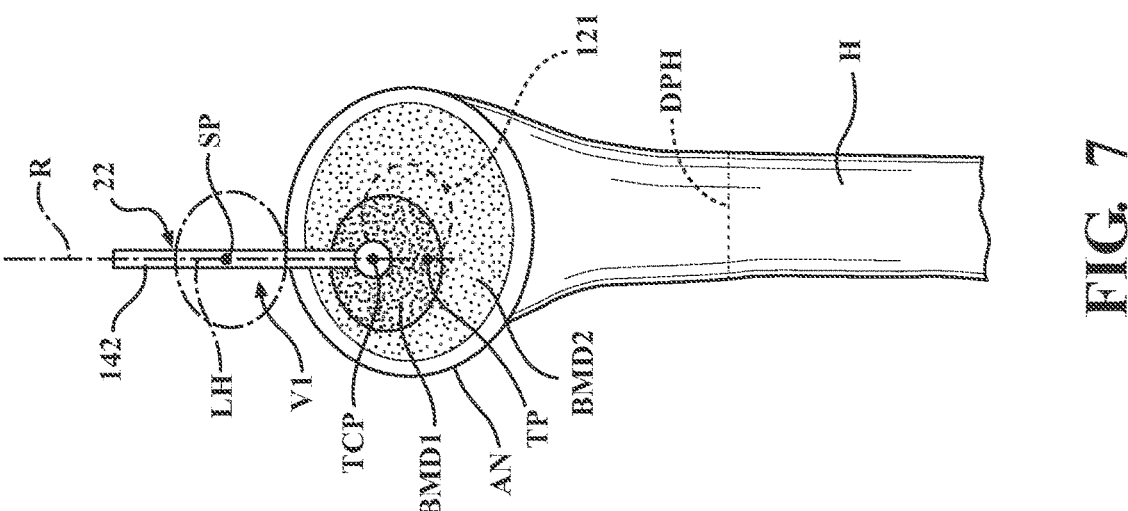
FIG. 7 is a top perspective view of the humerus of FIG. 6 illustrating a bur preparing to remove material from the humerus.
Figure 6:
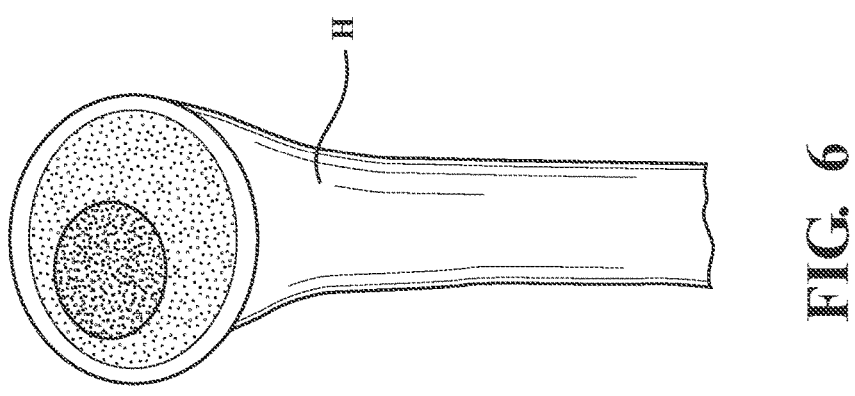
FIG. 6 is a top perspective view of a humerus having volumes of tissue of varying density.

Referring to FIGS. 6 through 8, once the humeral head HH has been resected, the humerus H is ready to be further prepared for receiving the humeral component 102 of the shoulder implant system 100. In some embodiments, one or more virtual objects that extend below the virtual resection plane could be used by the manipulator controller 54 to define a volume of material to be removed from the humerus H to receive the humeral component 102. The manipulator controller 54 is configured to operate the manipulator 56 to control movement of a drill, bur, saw blade, or other cutting tool, based on the one or more virtual objects. The one or more virtual objects may be sized so that a distal portion of the volume of material to be removed from the humerus H extends below the anatomical neck AN of the humerus and terminates above a diaphysis DPH of the humerus H (see FIG. 7) so that a substantial portion of a humeral canal remains intact after the humeral component 102 is fully seated in the humerus H.

The one or more virtual objects are registered to the coordinate system to which the pre-operative model is registered (or are defined in the pre-operative model) to define one or more virtual cutting boundaries for the surgical tool 22 so that the user is limited from removing more material than needed to accurately position the humeral component 102 securely within the humerus H. As previously described, the manipulator 56 may be operated in the haptic mode during cutting to generate haptic feedback to the user based on a position of the surgical tool 22 relative to the virtual cutting boundaries. For example, the manipulator 56 may be controlled by the manipulator controller 54 to generate haptic feedback in response to the working end of the surgical tool 22 reaching or exceeding a virtual cutting boundary defined by the virtual objects.

Owing to the attachment of the tracker 44 to the humerus H, the location of the working end of the surgical tool 22 relative to the humerus H can be visualized on the displays 28, 29, along with a visualization of the virtual objects. For instance, isometric, side, top, cross-sectional, or other views of the humerus H may be displayed with graphical representations of the virtual objects overlaid on the representation of the humerus H. Similarly, a representation of the working end of the surgical tool 22 can be displayed in relation thereto and updated so that the user is able to visualize, in substantially real-time, a pose of the surgical tool 22 relative to the humerus H and the associated virtual cutting boundaries.

During preparation of the humerus H in FIGS. 7 and 8, one virtual object V1 may be sized and shaped to correspond to an eccentric peg 116 of a proximal body 114 of the humeral component 102 to define the volume of material to be removed from the humerus H to form a pocket 118 sized to receive the eccentric peg 116. As shown in FIG. 7, the virtual object V1 may comprise a trajectory and be further defined as a line haptic object LH having the starting point SP and target point TP as described above. The eccentric peg 116 shown in FIG. 8 is merely one example of an eccentric distal projection of an implant component that could be employed. For instance, eccentrically located pegs, keels, and/or screws, and the like could be used.

In some embodiments, before forming the pocket 118, the robotic system 10 autonomously aligns the rotational axis R of the surgical tool 22 with the desired trajectory. Such autonomous positioning may be initiated by the user pulling a trigger on the surgical tool 22, or otherwise providing input to the robotic system 10 to start the movement. In some cases, a tool center point (TCP) of the surgical tool 22 is first brought to within a predefined distance of the starting point SP of the line haptic object LH that provides the desired trajectory (such as within a predefined starting sphere as shown). Once the TCP (e.g., bur centroid, drill tip center, etc.) is within the predefined distance of the starting point SP, then pulling the trigger (or alternatively pressing a foot pedal or actuating some other input) causes the manipulator 56 to autonomously align and position the surgical tool 22 on the desired trajectory. Once the surgical tool 22 is in the desired pose, the robotic system 10 may effectively hold the surgical tool 22 on the desired trajectory by tracking movement of the patient and autonomously adjusting the manipulator 56 as needed to keep the surgical tool 22 on the desired trajectory.

While the robotic system 10 holds the surgical tool 22 on the desired trajectory, the user may then manually manipulate the surgical tool 22 to move (or cause movement of) the drill or bur along the line haptic object LH (e.g., along the desired trajectory) toward the bone to form the pocket 118. In some cases, such as in the haptic mode, the robotic system 10 constrains the user's movement of the surgical tool 22 to stay along the desired trajectory by providing haptic feedback to the user should the user attempt to move the surgical tool 22 in a manner that deviates from the line haptic object LH and the desired trajectory. If the user desires to return the manipulator 56 to a free mode, for unconstrained movement of the surgical tool 22, the user can then pull the surgical tool 22 back along the line haptic object LH, away from the patient, until an exit point of the line haptic object LH is reached.

The virtual object (e.g., haptic object) used to constrain the user's movement along the desired trajectory may also indicate, such as via haptic feedback, when the user has reach the desired depth of the pocket 118, e.g., reached the target point TP. Separate virtual boundaries could also be used to set the desired depths. In other cases, the robotic system 10 may autonomously drill (e.g., bur) the pocket 118 to the desired depth. In further cases, the robotic system 10 may initially drill autonomously, but then final drilling may be done manually, or vice versa. Once the pocket 118 is created, the peg 116 can then be placed manually or with a driver of the surgical tool 22.

As illustrated in FIGS. 6 through 8, the tissue of the humerus H that lies below the resection likely has a varying bone mineral density (BMD) distribution. Accordingly, there are likely regions of higher density BMD1 and adjacent regions of relative lower density BMD2, e.g., less dense bone. With this in mind, during planning of the placement of the peg 116, such density distributions can be taken into account so that the peg 116 is placed in higher density material BMD1 to provide greater stability to the humeral component 102. More specifically, since the peg 116 is eccentrically located on the proximal body 114, the peg 116 is able to be placed along any point on placement circle 121 while allowing the proximal body 114 to remain centrally positioned on the humerus H. In other words, the placement circle 121 has a radius from a general center of the resection area that is the same or nearly the same as the radius of the peg 116 from a center of the proximal body 114. Accordingly, the robotic system 10 may be configured to determine, via a density distribution of the tissue, the location of highest density material BMD1 on the placement circle 121 and define the virtual object V1 at that location.

In order to determine the location of highest density material BMD1 on the placement circle 121, a BMD distribution first needs to be established for the bone to which the surgical tool 22 is to be applied. For example, if the surgical tool 22 is being used to remove material from the humerus H and the scapula S, separate BMD distributions should be determined for each of the humerus H and the scapula S. The BMD distribution may be determined preoperatively or intraoperatively.

BMD measuring systems and methods for determining BMD distributions for volumes of bone are known in the art. One example of a BMD measuring system and method is described in "VISBONE: 3D Visualization of Bone Mineral Density" by Choi et al. from the Pacific Conference on Computer Graphics and Applications, pages 138-146, IEEE Computer Society, (1999), hereby incorporated by reference. The densities measured by this BMD measuring system and method may be expressed in $g/cm^3$. BMD may also be determined using Quantitative Computed Tomography (QCT), which uses a standard Computed Tomography (CT) scanner with a calibration standard to convert Hounsfield Units (HU) of the CT image to BMD values.

The BMD distribution is provided as part of a 3-D representation or model of the bone that is generated by the BMD measuring system and stored in memory in the navigation controller 26 and/or the manipulator controller 54. The 3-D representation may comprise a plurality of voxels with the number of voxels being based on the desired resolution of the 3-D model. Point clouds with associated BMD values or other suitable BMD distribution methods may also be employed. Each voxel in the 3-D model (or groups/clusters of voxels as described below) is assigned a density based on the measurements taken of the tissue. The 3-D model is registered to the actual bone (or other coordinate system), such as the humerus H, so that as the bone moves during the surgery, the 3-D model also moves and is tracked by the guidance station 20 so that the robotic system 10 is able to track the location of the working end of the surgical tool 22 relative to the bone and relative to the voxels containing the density data. The densities for different clusters of adjacent voxels may also be averaged to determine a common BMD value for each of the different clusters. Similarly, the associated density values (or graphical depiction of density) could be provided to the user on the displays 28, 29. Accordingly, in the free mode, the user could move the surgical tool 22 to manually remove material based on the densities shown in the displays 28, 29 and the relative location of the surgical tool 22 relative to those densities, which are being display in essentially real-time.

Once the BMD distribution is determined and mapped to the placement circle 121, the manipulator controller 54 can evaluate the values of BMD on the placement circle 121 and select the location of the highest value as the location for the peg 116. Additionally, or alternatively, the manipulator controller 54 can consider BMD values below the placement circle (e.g., below the resection) to ensure that suitably dense material exists at the surface and also sufficiently deep enough below the surface to suitably hold the peg 116. Accordingly the manipulator controller 54 can evaluate each of the values for the voxels at the surface and below the surface to determine the zone of highest BMD values (which can include average values for groups/clusters of voxels). Once the manipulator controller 54 determines which region has the highest value(s), the manipulator controller 54 can then place the trajectory (e.g., the line haptic object LH) in the same coordinate system directly on the placement circle 121 at that location.

Referring to FIG. 8, one embodiment of the humeral component 102 is shown as comprising solely the proximal body 114 having a semi-spherical head 119 and the eccentric peg 116 extending downwardly from the head 119. The head 119 is shaped to provide an articulating surface shaped to engage a corresponding articulating surface of the glenoid component 104 described further below. The proximal body 114 may be formed of metal, such as any suitable metal implant material, plastic material, combinations thereof, and the like.

Figure 9:
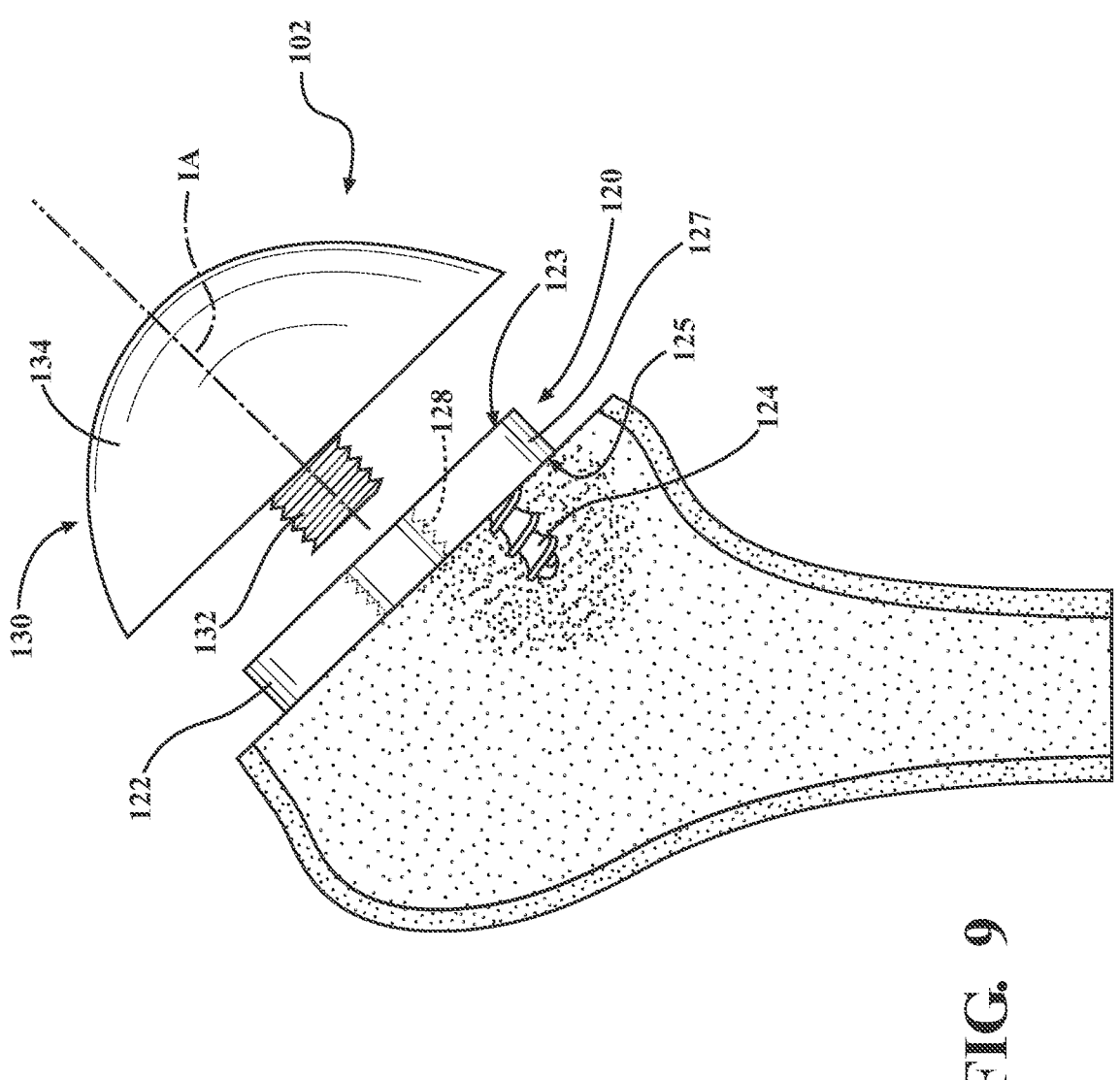
FIG. 9 is an illustration of an eccentric distal projection placed in the volume of tissue having a relatively higher density, the eccentric distal projection configured to receive a proximal body.

In the embodiment of FIG. 9, the humeral component 102 further comprises a distal body 120. The distal body 120 comprises a base flange 122 and a peg 124 depending downwardly from the base flange 122. In this embodiment, the peg 124 is eccentrically located in the same manner as the peg 116 for purposes of providing flexibility in placement of the peg 124 in the tissue so that the peg 124 can be located in suitably dense bone, while maintaining suitable positioning of the humeral component 102 (e.g., to cover the resection).

A bore 128 is defined in the base flange 122 to receive a central post 132 of an alternative proximal body 130. The alternative proximal body 130 further has a semi-spherical head 134 and the central post 132 depends centrally from the head 134. The post 132 may be connected to the base flange 122 by a threaded connection, taper lock, etc. In the embodiment shown, the bore 128 is centrally located in the distal body 120, but could be eccentrically located in other embodiments. The bore 128 may be threaded or may otherwise have coupling features to engage the post 132 (e.g., Morse taper, threads, etc.) and secure the proximal body 130 to the distal body 120. The distal body 120 may be formed of metal, such as any suitable metal implant material, plastic material, combinations thereof, and the like.

The base flange 122 includes a proximal end surface 123, a distal bone-engaging surface 125, and a side flange surface 127. Proximal end surface 123 may be flat as shown, but in other embodiments it may be inclined or sloped. Side flange surface 127 may have a uniform height, the height measured from distal to proximal ends of side flange surface 127, or the height may vary along proximal end surface 123. Distal bone-engaging surface 125 may include a porous surface, for example porous titanium alloy, across all or a portion of its surface to provide better fixation of the implanted base flange 122 with bone.

The bore 128 may extend distally along implant axis IA from proximal end surface 123 of base flange 122. The bore 128 may extend only partially into the distal body 120 along the implant axis IA or it may extend entirely through the distal body 120 and define a throughbore. The post 132 of the proximal body 114 may be placed within the bore 128 and attached thereto. The proximal body 114 (e.g., humeral head component) may be attached by any known securement methods including screw or friction fit. The distal body 120 may include additional holes for use with insertion/extraction tools and/or for accepting sutures.

Figures 10, 11, 12:
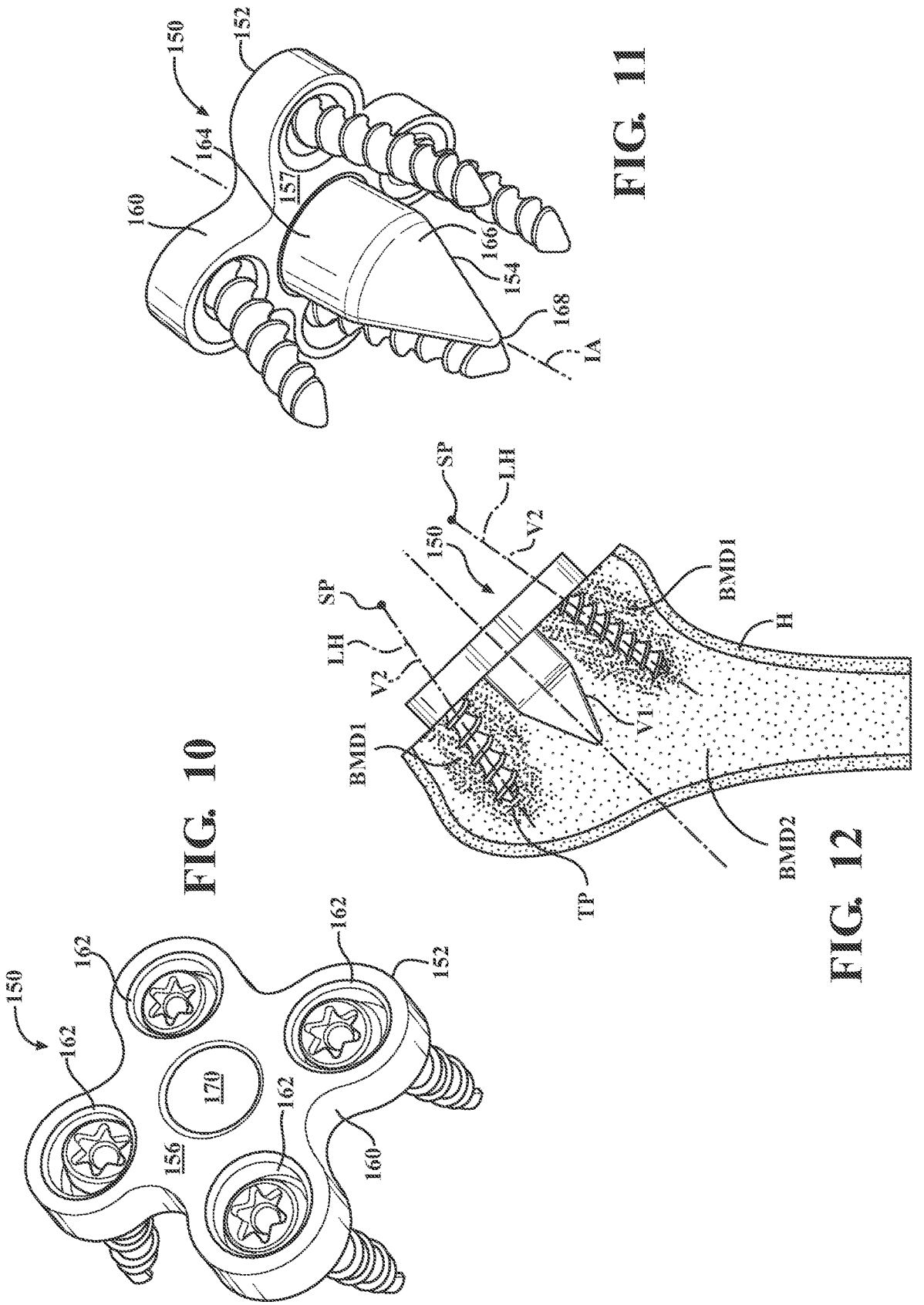
FIG. 10 is a top perspective view of another distal body to be placed in the humerus.
FIG. 11 is a bottom perspective view of the distal body of FIG. 10.
FIG. 12 is an illustration of the distal body of FIG. 10 being placed in the humerus with one or more fasteners being located in volumes of tissue having relatively higher densities.

Referring to FIGS. 10 and 11, an alternative distal body 150 (also referred to as a base) is shown. Distal body 150 includes base flange 152 coupled with a central anchor 154. The base flange 152 may have a generally rounded cruciform shape, although in other examples, the base flange 152 may have other shapes including oblong or annular. The base flange 152 includes a proximal end surface 156, a distal bone-engaging surface 157, and a side base flange surface 160. Proximal end surface 156 may be flat as shown, but in other embodiments it may be inclined or sloped. Side base flange surface 160 may have a uniform height, the height measured from distal to proximal ends of side base flange surface 160, or the height may vary along proximal end surface 156. Distal bone-engaging surface 157 may include a porous surface, for example porous titanium alloy, across all or a portion of its surface to provide better fixation of the implanted distal body 150 with the bone.

Base flange 152 includes at least one hole 162 extending from proximal end surface 156 to distal bone-engaging surface 157. The holes 162 are each adapted to receive a screw. In the illustrated embodiment, there are four holes 162 and four screws, although there can be more or fewer holes and/or screws. The screws may be variable angle locking screws capable of being inserted through holes 162 at variable angles, with the heads of the screws having locking threads to mate with corresponding locking threads in the holes. The screws may engage the bone to provide fixation of the distal body 150 in the bone. The screws may have varying lengths to accommodate bone purchase to help with fixation, although any combination of screw lengths may be appropriate.

The distal body 150 includes central anchor 154 coupled to the base flange 152 at a first end and extending distally from the base flange 152 along the implant axis IA to a second end. In the illustrated embodiment, the central anchor 154 has a straight portion 164, which may be cylindrical, and a tapered portion 166, which may be conical or frustoconical. Tapered portion 166 is tapered along the implant axis IA so that the proximal end of the tapered portion 166 has a relatively large diameter, with the diameter of the central anchor 154 generally narrowing toward second end until the central anchor terminates in distal tip 168.

As with previous embodiments, the distal body 150 may further define an opening 170. Opening 170 may extend distally along the implant axis IA from proximal end surface 156 of base flange 152. Opening 170 may extend partially or fully through the central anchor 154 along the implant axis IA or it may be shallow and extend only into base flange 152. The proximal body 114 may be placed within opening 170 and attached thereto, for example by threads, a taper lock such as a Morse taper, or the like. The proximal body 114 may be attached by any known securement means including screw or friction fit. The distal body 150 may include additional holes for use with insertion/extraction tools and/ or for accepting sutures. FIG. 12 shows the distal body 150 implanted within the humerus H with variable angle locking screws.

During preparation of the humerus H, one virtual object V1 may be sized and shaped to correspond to the anchor 154 to define the volume of material to be removed from the humerus H to receive the central anchor 154. One or more secondary virtual objects V2 may be sized and shaped to correspond to pilot holes to be placed in the humerus H for the one or more variable angle locking screws. The virtual objects V1, V2 may comprise trajectories, such as line haptic objects LH. These secondary virtual objects V2 can be located in much the same manner as the virtual objects described above with respect to FIGS. 7 through 9, i.e., by determining locations of higher density material BMD1 in which to place the screws to further ensure that the screws hold the distal body 150 in place. Accordingly, surgical planning can be carried out as previously described, with the BMD distribution first being determined, the locations of the screws and associated openings 162 being based on the BMD distribution, and thus the rotational orientation of the distal body 150 relative to the humerus H being determined based on the desired locations of the screws and the openings 162.

Figures 13, 14:
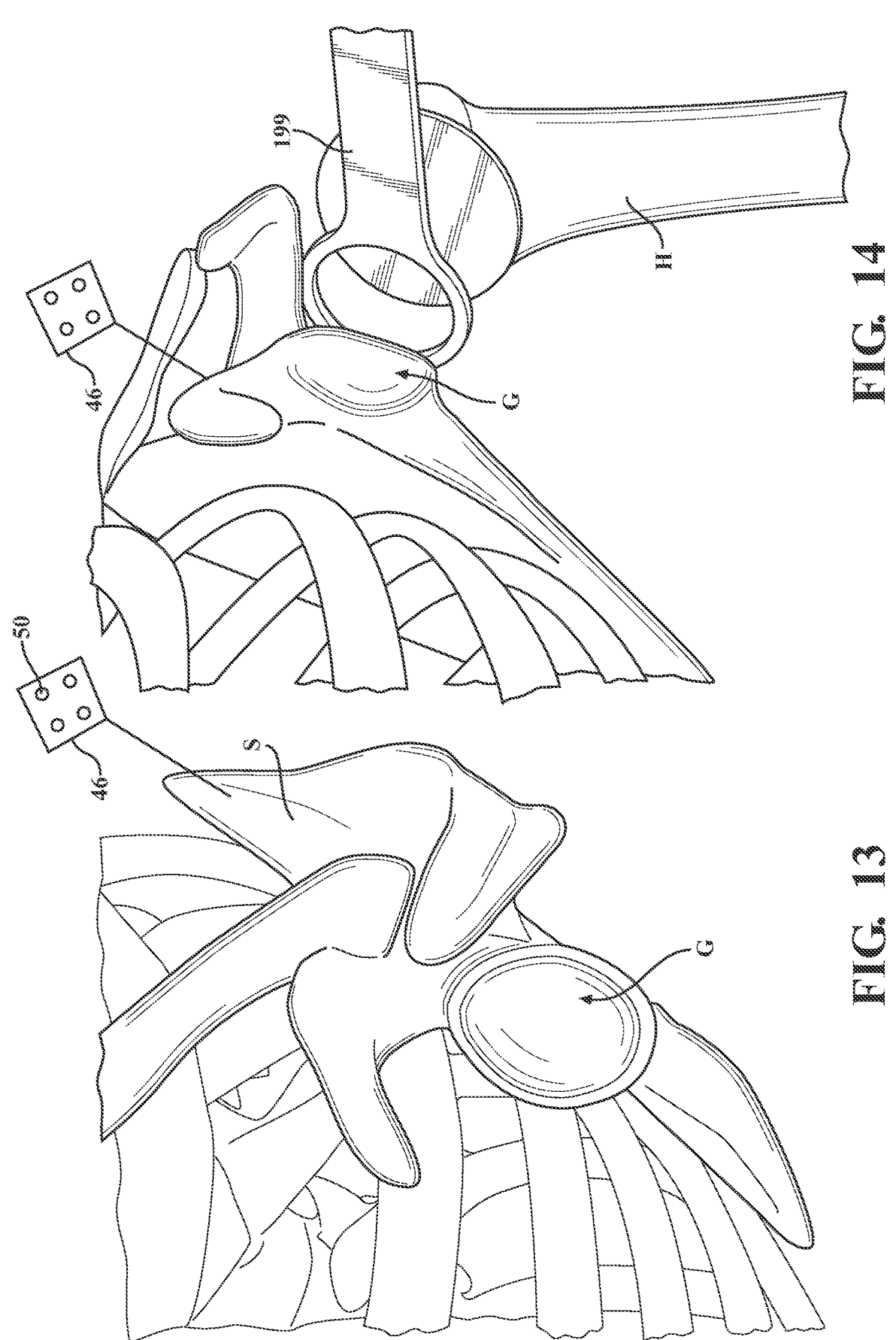
FIGS. 13-18 illustrate various steps taken to prepare a glenoid cavity of the shoulder joint to receive a glenoid component of the shoulder implant system.

Referring to FIGS. 13 through 18, preparation of the glenoid cavity G is illustrated. Preparation of the glenoid cavity G may comprise a combination of manual and robotic operations such as drilling, reaming, burring, and the like. As previously described, glenoid preparation can be done at any time in the procedure, and can be done immediately following humeral head HH resection, but before placement of the humeral component 102, after placement of the humeral component 102, or before preparation of the humerus H. In FIGS. 13 and 14, a retractor 199 is used to retract the humerus H and expose the glenoid cavity G.

Figures 15, 16:
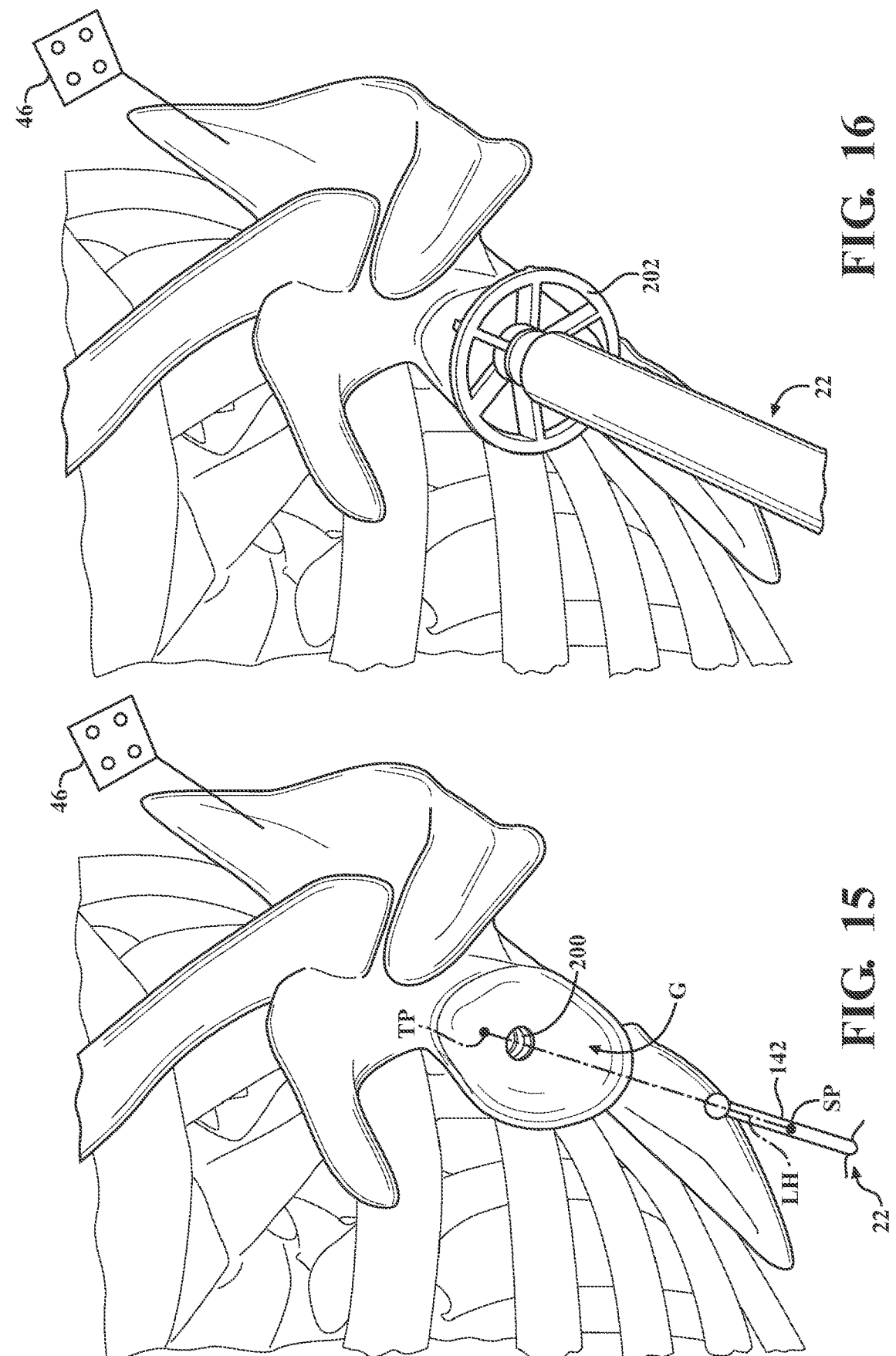

Referring to FIG. 15, a center hole 200 is first prepared through the glenoid cavity G. The center hole 200 may be defined by a virtual object, such as a line haptic object LH that defines the trajectory and stopping location for the center hole 200. A bur, drill or other accessory may be used in the surgical tool 22 to form the center hole 200 in the free mode (using visualization of the desired trajectory and depth as a guide), in the haptic mode (using haptic feedback to keep the surgical tool 22 on the trajectory and at a suitable depth), or in the semi-autonomous mode in which the manipulator 56 moves the surgical tool 22 autonomously along the trajectory to prepare the center hole 200 at the desired depth.

Owing to the attachment of the tracker 46 to the scapula S, the location of the working end of the surgical tool 22 relative to the glenoid cavity G can be visualized on the displays 28, 29, along with a visualization of the virtual object, such as the line haptic object LH. For instance, isometric, side, top, cross-sectional, or other views of a representation of the glenoid cavity G may be displayed with virtual representations of the line haptic object LH overlaid on the representation of the glenoid cavity G. Similarly, a representation of the working end of the surgical tool 22 can be displayed in relation thereto and updated so that the user is able to visualize, in substantially real-time, a pose of the surgical tool 22 relative to the glenoid cavity G and the associated virtual line haptic object LH, which also defines a virtual cutting boundary for the surgical tool 22.

Referring to FIG. 16, once the center hole 200 is prepared, an appropriately sized reamer head 202 can be used on the surgical tool 22 to contour the glenoid cavity G to provide a desired contoured surface for receiving the glenoid component 104. The reamer head 202 has a distally protruding centering pin (not shown) that is seated in the center hole 200 to center the reamer head 202 and at least partially orient the reamer head 202 during reaming operations. Another virtual object may also be associated with the desired contoured surface of the glenoid cavity G so that the reamer head 202 is limited from penetrating beyond the desired contoured surface. As a result, in some versions, the center hole 200 may not be needed to locate the centering pin of the reamer head 202 as the manipulator 56 controls the location of the reamer head 202 based on the associated contoured surface virtual object. In some embodiments, a bur is used to shape/contour the glenoid cavity G to receive the glenoid component 104.

Figures 17, 18:
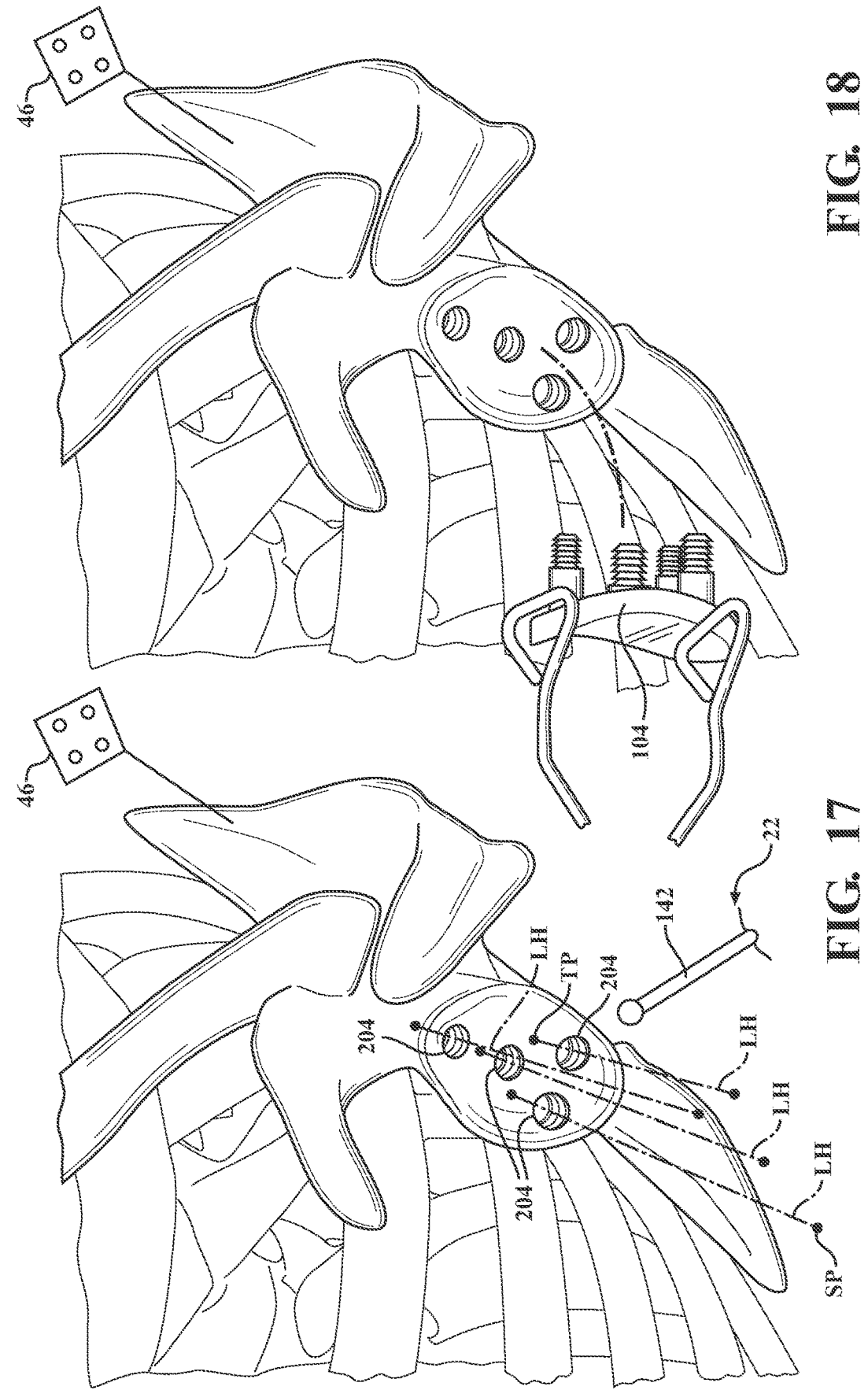

Referring to FIG. 17, peg holes 204 can be formed through the glenoid cavity G similar to the center hole 200. Each of the peg holes 204 may be defined by a virtual object, such as a line haptic object LH that defines the trajectory and stopping location for the peg hole 204. A bur, drill or other accessory may be used in the surgical tool 22 to form the peg holes 204 in the free mode (using visualization of the desired trajectory and depth as a guide), in the haptic mode (using haptic feedback to keep the surgical tool 22 on the trajectory and at a suitable depth), or in the semi-autonomous mode in which the manipulator 56 moves the surgical tool 22 autonomously along the trajectory to prepare the peg holes 204 at the desired depths. In some embodiments, one or more of the virtual objects may be active at a given time, inactive, or combinations thereof. For example, when preparing the peg holes 204, multiple, separate line haptic objects LH defining the desired trajectories are employed, but only one or more of them may be active at any given time so that the user and/or the manipulator 56 is able to focus on preparing one peg hole at a time. With only one line haptic object LH being active, then the manipulator 56 is able to lock the surgical tool 22 on that line haptic object LH without inadvertently locking onto a different, adjacent line haptic object. The user can also manually select, via the user interface for the navigation controller 26, which peg hole is to be prepared and the robotic system 10 can activate the associated line haptic object LH accordingly.

Referring to FIG. 18, once the peg holes 204 are formed, the glenoid component 104 can be placed in the glenoid cavity G and secured by press-fit, bone cement or other adhesive, screws, or otherwise.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A robotic surgery system for preparing a bone to receive a stemless implant having a proximal body defining a center axis and an eccentric distal projection configured for attachment to the bone, wherein the eccentric distal projection is offset from the center axis by a non-zero offset distance, the robotic surgery system comprising:

a robotic manipulator;

a cutting tool to be coupled to the robotic manipulator;

a localizer configured to track movement of the cutting tool and the bone; and a controller coupled to the robotic manipulator and the localizer, the controller configured to:

operate the robotic manipulator to control movement of the cutting tool relative to the bone to resect the bone and to expose a resected bone area;

determine, based on density data of the bone, a first region of cancellous bone of the resected bone area and an adjacent second region of cancellous bone of the resected bone area, wherein the first region has a greater density than the second region;

identify, relative to the resected bone area, a virtual placement circle having a radius corresponding to the offset distance, wherein a plurality of locations are defined along the placement circle, and wherein when the eccentric distal projection is placed at any of the plurality of locations along the placement circle, the proximal body is configured to remain centrally positioned on and configured to cover the resected bone area;

define a virtual object relative to the resected bone area, wherein the virtual object is located on the virtual placement circle and within the first region of cancellous bone of the resected bone area; and operate the robotic manipulator to control movement of the cutting tool based on the virtual object to remove additional material from the resected bone area to enable placement of the eccentric distal projection within the first region of cancellous bone of the resected bone area.

2. The robotic surgery system of claim 1, wherein the controller is configured to register a coordinate system to the bone.

3. The robotic surgery system of claim 2, wherein the controller is configured to:

define a virtual resection plane in the coordinate system;

operate the robotic manipulator to control the movement of the cutting tool relative to the bone to resect the bone along the virtual resection plane to expose the resected bone area; and define the virtual object in the coordinate system based on a location of the virtual resection plane such that the virtual object extends below the virtual resection plane in the coordinate system.

4. The robotic surgery system of claim 3, wherein the controller is configured to determine positions of a plurality of landmarks on the bone.

5. The robotic surgery system of claim 4, wherein the controller is configured to define the virtual resection plane based on the positions of the plurality of landmarks.

6. The robotic surgery system of claim 1, wherein:

the controller is configured to operate the robotic manipulator to control the movement of the cutting tool based on the virtual object to remove the additional material from the resected bone area to enable the placement of the eccentric distal projection to fully seat the stemless implant in the bone, and the virtual object is sized so that a distal portion of the additional material to be removed from the resected bone area is configured to extend below an anatomical neck of the bone and is configured to terminate above a diaphysis of the bone so that a substantial portion of a canal of the bone is configured to remain intact after the stemless implant is fully seated in the bone.

7. The robotic surgery system of claim 1, wherein the virtual object comprises a virtual cutting boundary.

8. The robotic surgery system of claim 7, wherein the robotic manipulator is configured to generate haptic feedback to a user based on a position of the cutting tool relative to the virtual cutting boundary.

9. The robotic surgery system of claim 8, wherein the virtual object comprises a trajectory having a starting point and a target point.

10. The robotic surgery system of claim 9, wherein the robotic manipulator is configured to generate the haptic feedback to the user in response to the cutting tool reaching the target point along the trajectory.

11. The robotic surgery system of claim 7, wherein the robotic manipulator is operable in a haptic mode in which the cutting tool is configured to be manually manipulated by a user and the robotic manipulator generates haptic feedback in response to the cutting tool reaching or exceeding the virtual cutting boundary.

12. The robotic surgery system of claim 7, wherein the robotic manipulator is operable in a free mode in which the cutting tool is configured to be freely manipulated by a user beyond the virtual cutting boundary.

13. The robotic surgery system of claim 1, wherein the robotic manipulator is operable in an autonomous mode in which the controller operates the robotic manipulator to control movement of the cutting tool autonomously along a tool path.

14. The robotic surgery system of claim 1, wherein the cutting tool comprises a saw blade.

15. The robotic surgery system of claim 1, wherein the cutting tool comprises a bur.

16. The robotic surgery system of claim 1, wherein the cutting tool comprises a drill.

17. The robotic surgery system of claim 1, wherein the density data of the bone includes bone mineral density distribution data determined preoperatively.

18. The robotic surgery system of claim 1, wherein the density data of the bone includes bone mineral density distribution data determined intraoperatively.

19. A method of operating a robotic surgery system for preparing a bone to receive a stemless implant having a proximal body defining a center axis and an eccentric distal projection configured for attachment to the bone, wherein the eccentric distal projection is offset from the center axis by a non-zero offset distance, the robotic surgery system including a robotic manipulator, a cutting tool to be coupled to the robotic manipulator, a localizer configured to track movement of the cutting tool and the bone, and a controller coupled to the robotic manipulator and the localizer, the method comprising the controller performing the steps of:

operating the robotic manipulator for controlling movement of the cutting tool relative to the bone to resect the bone and to expose a resected bone area;

determining, based on density data of the bone, a first region of cancellous bone of the resected bone area and an adjacent second region of cancellous bone of the resected bone area, wherein the first region has a greater density than the second region;

identifying, relative to the resected bone area, a virtual placement circle having a radius corresponding to the offset distance, wherein a plurality of locations are defined along the placement circle, and wherein when the eccentric distal projection is placed at any of the plurality of locations along the placement circle, the proximal body is configured to remain centrally positioned on and configured to cover the resected bone area;

defining a virtual object relative to the resected bone area, wherein the virtual object is located on the virtual placement circle and within the first region of cancellous bone of the resected bone area; and operating the robotic manipulator for controlling movement of the cutting tool based on the virtual object to remove additional material from the resected bone area to enable placement of the eccentric distal projection within the first region of cancellous bone of the resected bone area.

* * * * *